US006734204B1

(12) United States Patent
Boger

(10) Patent No.: US 6,734,204 B1
(45) Date of Patent: *May 11, 2004

(54) SEROTONIN POTENTIATION BY OLEAMIDE ANALOGS

(75) Inventor: Dale L. Boger, La Jolla, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/647,447
(22) PCT Filed: Apr. 30, 1999
(86) PCT No.: PCT/US99/09617
§ 371 (c)(1),
(2), (4) Date: Sep. 28, 2000

Related U.S. Application Data

(63) Continuation-in-part of application No. 09/071,389, filed on Apr. 30, 1998.

(51) Int. Cl.$^7$ ............................................. A61K 31/40
(52) U.S. Cl. ..................... 514/408; 514/422; 514/423; 514/475; 514/613; 514/616; 514/617; 514/619; 514/620; 514/621; 514/622; 514/625; 514/626; 514/627; 514/702; 514/703; 514/704; 514/705
(58) Field of Search ................................. 514/408, 422, 514/423, 475, 613, 616, 617, 619, 620, 621, 622, 702, 625, 626, 627, 703, 704, 705

(56) References Cited

U.S. PATENT DOCUMENTS 5,612,380 A 3/1997 Lerner et al.

OTHER PUBLICATIONS

Lerner, et al., "Cerebrodiene: A Brain Lipid Isolated from Sleep–Deprived Cats", Proc. Natl. Acad. Sci. USA 91: 9505–9508 (1994).
Koutek, et al., "Inhibitors of Arachidonyl Ethanolamide Hydrolysis", J. Biol. Chem. 269: 22937–22940 (1994).
Cravatt, et al., "Chemical Characterization of a Family of Brain Lipids that Induce Sleep", Science 268: 1506–1509 (1995).
Cravatt, et al., "Structure Determination of an Endogenous Sleep–Inducing Lipid, cis–9–Octadecenamide (Oleamide): A Synthetic Approach to the Chemical Analysis of Trace Quantities of a Natural Product", J. Am. Chem. Soc. 118: 580–590 (1996).
Merkler, et al., "Fatty Acid Amide Biosynthesis: A Possible New Role for Peptidylglycine α–Amidating Enzyme and Acyl–Coenzyme A: Glycine N–Acyltransferase", Arch. Biochem. Biophys. 330: 430–434 (1996).
Patterson, et al., "Inhibition of Oleamide Hydrolase Catalyzed Hydrolysis of the Endogenous Sleep–Inducing Lipid cis–9–Octadecenamide", J. Am. Chem. Soc. 118: 5938–5945 (1996).

Huidobro–Toro, et al., "Brain Lipids that Induce Sleep are Novel Modulators of 5–Hydroxytryptamine Receptors", Proc. Natl. Acad. Sci. USA 93: 8078–8082 (1996).
Cravatt, et al., "Molecular Characterization of an Enzyme that Degrades Neuromodulatory Fatty–Acid Amides", Nature 384: 83–87 (1996).
De Petrocellis, et al., "Novel Inhibitors of Brain, Neuronal, and Basophilic Anandamide Amidohydrolase", Biochem. Biophys. Res. Commun. 231: 82–88 (1997).
Deutsch, et al., "Methyl Arachidonyl Fluorophosphonate: A Potent Irreversible Inhibitor of Anandamide Amidase", Biochem. Pharmacol. 53: 255–260 (1997).
Giang, et al., "Molecular Characterization of Human and Mouse Fatty Acid Amide Hydrolases", Proc. Natl. Acad. Sci. USA 94: 2238–2242 (1997).
Thomas, et al., "Fatty Acid Amide Hydrolase, the Degradative Enzyme for Anandamide and Oleamide, Has Selective Distribution in Neurons Within the Rat Central Nervous System", J. Neuroscience Res. 50: 1047–1052 (1997).
Lerner, "A Hypothesis about the Endogenous Analogue of General Anesthesia", Proc. Natl. Acad. Sci. USA 94:13375–13377 (1997).
Thomas, et al., "Unique Allosteric Regulation of 5–Hydroxytryptamine Receptor–Mediated Signal Transduction by Oleamide", Proc. Natl. Acad. Sci. USA 94: 14115–14119 (1997).

Primary Examiner—Frederick Krass
(74) Attorney, Agent, or Firm—Donald G. Lewis

(57) ABSTRACT

Analogs related to oleamide are employed for potentiating the 5-HT$_{2A}$ and 5-HT$_{1A}$ responses to serotonin (5-HT). With respect to the potentiation of the 5-HT$_{2A}$ receptor response, it is disclosed that, of the naturally occurring fatty acids, the primary amide of oleic acid (oleamide) is the most effective potentiating agent of serotonin and that the potentiating activity of oleamide analogs is highly dependent upon their structural features. In particular, the presence, position, and stereochemistry of the 9-cis double bond is required and even subtle structural variations reduce or eliminate activity. Secondary or tertiary amides may replace the primary amide but follow a well-defined relationship requiring small amide substituents suggesting that the carboxamide serves as a hydrogen bond acceptor but not donor. Alternative modifications at the carboxamide as well as modifications of the methyl terminus or the hydrocarbon region spanning the carboxamide and double bond typically eliminate activity. With respect to the potentiation of the 5-HT$_{1A}$ receptor response, it is disclosed that the potentiation activity of oleamide analogs is more tolerant and accommodates a wider range of structural modifications. One genus of analogs is disclosed that inhibits rather than potentiates the 5-HT$_{2A}$, but not the 5-HT$_{1A}$, receptor response. Such analogs permit the selective modulation of serotonin receptor subtypes and have opposing effects on the different subtypes.

10 Claims, 11 Drawing Sheets

| notation[a] | rel % potentiation | |
|---|---|---|
| | 5-HT$_{2A}$ | 5-HT$_{1A}$ |
| 18:0 (stearamide) | 0% | 32% |
| one double bond | | |
| 14:1$^9$ (myristoleamide) | -36% | 66% |
| 16:1$^9$ (paimitoleamide) | -16% | 88% |
| 17:1$^8$ | 28% | |
| 18:1$^6$ | -48% | |
| 18:1$^7$ | 32% | |
| 18:1$^8$ | 36% | 27% |
| 18:1 (oleamide) | 100% | 100% |
| 18:1$^{9-trans}$ (elaidamide) | 0% | 20% |
| 18:1$^{12}$ | 44% | |
| 18:1$^{13}$ | 4% | |
| 18:1$^{15}$ | 0% | |
| 19:1$^{10}$ | 0% | |
| 20:1$^5$ | -60% | |
| 20:1$^8$ | 0% | |
| 20:1$^9$ | 0% | |
| 20:1$^{11}$ | 0% | |
| 20:1$^{13}$ | 32% | |
| 22:1$^9$ | 0% | |
| 22:1$^{13}$ (erucamide) | 16% | |
| 24:1$^9$ | 0% | |
| 24:1$^{15}$ (nervonamide) | 12% | |
| two double bonds | | |
| 18:2$^{9,12}$ (linoleamide) | 44% | 96% |
| 18:2$^{9,12-trans}$ (linoelaidamide) | 0% | |
| 20:2$^{11,14}$ | 50% | |
| three double bonds | | |
| 18:3$^{6,9,12}$ (γ-linolenamide) | 60% | |
| 18:3$^{9,12,15}$ (α-linolenamide) | 36% | |
| 20:3$^{8,11,14}$ | 28% | |
| 20:3$^{11,14,17}$ | 48% | |
| four double bonds | | |
| 20:4$^{5,8,11,14}$ (arachidonamide) | 0% | |
| five double bonds | | |
| 20:5$^{5,8,11,14,17}$ | 36% | |
| six double bonds | | |
| 22:6$^{4,7,10,13,16,19}$ | 25% | |

FIG. 3

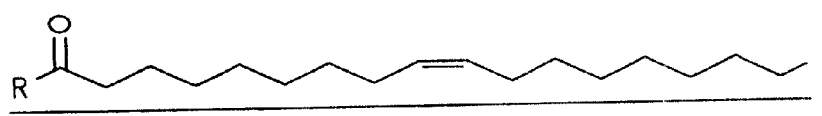
| agent (R) | rel % potentiation | |
|---|---|---|
| | 5-HT$_{2A}$ | 5-HT$_{1A}$ |
| NH$_2$ (oleamide) | 100% | 100% |
| MeNH | 133% | 213% |
| Me$_2$N | 156% | |
| EtNH | 136% | |
| Et$_2$N | 112% | |
| CH$_2$=CHCH$_2$NH | 56% | |
| PrNH | 0% | |
| i-PrNH | 0% | 100% |
| i-PrNMe | 0% | |
| BuNH | -8% | |
|  | 0% | |
| PhNH | -4% | |
|  | -72% | 145% |
| HONH | 81% | 15% |
| MeONMe | 68% | |
| NH$_2$NH | 0% | |
FIG. 4

| agent (R) | rel % potentiation | |
|---|---|---|
| | 5-HT2A | 5-HT1A |
| NH2 (oleamide) | 100% | 100% |
| OH (oleic acid) | 0% | 16% |
| OMe | −28% | |
| OEt | −24% | |
| OPr | 0% | |
| OCH2CHMe2 | 0% | |
| H | 0% | 81% |
| CF3 | 8% | 46% |
| CH2Cl | 12% | |
| CH2Br | 0%[a] | |
| CHN2 | −36% | |

| agent (R) | rel % potentiation |
|---|---|
| | 5-HT2A |
| CH2OH | 0% |
| CH2OAc | 0% |
| CH2NH2 | 0% |
| CH(OMe)2 | 0% |

[a]Toxic to cells

FIG. 5

| agent (R) | rel % potentiation | |
| --- | --- | --- |
| | 5-HT2A | 5-HT1A |
| NH2 (oleamide) | 100% | 100% |
| HOCH2CH2NH | 0% | 112% |
| HOCH2CH2CH2NH | 0% | 106% |
| (HOCH2CH2)2N | 0% | |
| HOCH2CH(OAc)CH2O | -32% | |

| agent (R) | rel % potentiation | |
| --- | --- | --- |
| | 5-HT2A | 5-HT1A |
| NH2 | 0% | |
| HOCH2CH2NH | -36% | 89% |
| (HOCH2CH2)2N | -28% | |

FIG. 6

| 5-HT conc | rel % response, oleamide conc[a] | | | |
|---|---|---|---|---|
| (mM) | 1 mM | 0.1 mM | 0.01 mM | 0.001 mM |
| 0.01 | 170 | 235 | 120 | 105 |
| 0.1 | 560 | 370 | 150 | 120 |
| 1.0 | 210 | 145 | | |
| 10 | 113 | 107 | | |
| 100 | 103 | 94 | | |

FIG. 11A

| 5-HT conc | rel % response, oleamide conc[a] | | | |
|---|---|---|---|---|
| (mM) | 1 mM | 0.1 mM | 0.01 mM | 0.001 mM |
| 0.01 | 150 | 120 | 100 | 105 |
| 0.1 | 140 | 165 | 100 | 120 |
| 1.0 | 170 | 170 | | |
| 10 | 85 | 90 | | |

SEROTONIN POTENTIATION BY OLEAMIDE ANALOGS

CROSS-REFERENCE TO RELATED APPLICATIONS

This is a US national phase application of international application Ser. No. PCT/US99/09617, filed Apr. 30, 1999 and published in English, which claims priority under 35 U.S.C. § 120 from and is a continuation-in-part application of U.S. patent application Ser. No. 09/071,389, filed Apr. 30, 1998.

TECHNICAL FIELD

The present invention relates to the use of oleamide based analogs that potentiate serotonin receptor subtypes. Some of the analogs are more potent agonists than oleamide and some of the analogs possess dual agonist/antagonist activity. Such analogs may permit selective modulation of or even have opposing effects on different serotonin receptor subtypes.

BACKGROUND

Oleamide (1) is an endogenous fatty acid primary amide that accumulates in the cerebrospinal fluid under conditions of sleep deprivation and induces physiological sleep in animals (Cravatt et al. (1995) Science 268, 1506–1509; Lerner et al. (1994) Proc. Natl. Acad. Sci. USA 91, 9505–9508; Cravatt et al. (1996) J. Am. Chem. Soc. 118, 580–590). Consistent with its role as a prototypical member of a new class of biological signaling molecules, enzymatic regulation of the endogenous concentrations of oleamide has been described or proposed (Patterson et al. (1996) J. Am. Chem. Soc. 118, 5938–5945; Cravatt et al. (1996) Nature 384, 83–87; Giang et al. Proc. Natl. Acad. Sci. USA 94, 2238–2242; Thomas et al. (1997) J. Neuroscience Res. 50, 1–6; Merkler et al. (1996) Arch. Biochem. Biophys. 330, 430–434).

Fatty acid amide hydrolase (FAAH) is an integral membrane protein that degrades 1 to oleic acid and potent inhibitors of the enzyme have been detailed (Koutek et al. (1994) J. Biol. Chem. 269, 22937–22940; Petrocellis et al. (1997) Biochem. Biophys. Rsch. Commun. 231, 82–88; Deutsch et al. (1997) Biochem. Pharmacol. 53, 255–260). The characterization and neuronal distribution of FAAH have been disclosed and the enzyme was found to possess the ability to hydrolyze a range of fatty acid amides including anandamide which serves as an endogenous ligand for the cannabinoid receptor (Devane et al. (1992) Science 258, 1946–1949; Di Marzo et al. (1995) Prostaglandins, Leukot. Essent. Fatty Acids 53, 1–11). Unlike anandamide, an appealing feature of this new class of biological signaling agents is the primary amide suggesting that their storage and release may be controlled in a manner analogous to that of peptide hormones terminating in a primary amide.

Recent studies have shown the oleamide modulates serotonergic neurotransmission (Huidobro-Toro et al. (1996) Proc. Natl. Acad. Sci. USA 93, 8078–8082; Thomas et al. (1997) Proc. Natl. Acad. Sci. USA 94, 14115–14119). In the first disclosure of such effects, oleamide was shown to potentiate 5-$HT_{2C}$ and 5-$HT_{2A}$ receptor-mediated chloride currents in transfected frog oocytes, but not those elicited by the 5-$HT_3$ ion-gated channel receptor or other G protein coupled receptors. This potentiation was greatest for the 5-$HT_{2C}$ receptor subtype where the effect was observed at concentrations as low as 1 nM and was maximal at 100 nM oleamide. Oleamide did not alter the serotonin (5-HT) $EC_{50}$ but instead increased receptor efficacy.

Similarly, oleamide has been reported to potentiate phosphoinositide hydrolysis in rat pituitary P11 cells expressing the 5-$HT_2$ receptor but to inhibit 5-$HT_7$ receptor-mediated stimulation of cAMP levels in HeLa cells transfected with the receptor. In these efforts, oleamide was shown to act as a weak agonist at the 5-$HT_7$ receptor but to behave as an unsurmountable antagonist in the presence of serotonin illustrating that it may act at an allosteric site (Huidobro-Toro et al. (1996) Proc. Natl. Acad. Sci. USA 93, 8078–8082; Thomas et al. (1997) Proc. Natl. Acad. Sci. USA 94, 14115–14119). Thus, oleamide has been shown to enhance (5-$HT_{2A}$, 5-$HT_{2C}$), disrupt (5-$HT_7$), or have no effect (5-$HT_3$) on serotonergic signal transduction at various receptor subtypes. Serotonin receptors have been implicated in anxiety, depression, appetite, thermoregulation as well as sleep and mood regulation and strong links between 5-$HT_1$, 5-$HT_2$, and 5-$HT_7$, and the regulation of sleep have been disclosed (Leonard et al. (1996) Psychother. Psychosom. 65, 66–75; Lovenberg et al. (1993) Neuron 11, 449–458).

What is needed are analogs which possess inhanced activity and selectivity over that of oleamide for the potentiation of serotonergic signal transduction at various receptor subtypes.

SUMMARY OF THE INVENTION

The invention is directed to the use of analogs which potentiate serotonin receptor subtypes. Many of the analogs are more potent agonists than oleamide and some of the analogs possess dual agonist/antagonist activity. Such analogs may permit selective modulation of or even have opposing effects on different serotonin receptor subtypes.

One aspect of the invention is directed to a method for selectively potentiating a cell having a serotonin receptor subtype 5-$HT_{1A}$. The method employs the step of contacting the cell having the serotonin receptor subtype 5-$HT_{1A}$ with a quantity of serotonergic agent possessing 5-$HT_{1A}$ agonist activity sufficient for potentiating said cell. Preferred serotonergic agents include compounds represented by the structure:

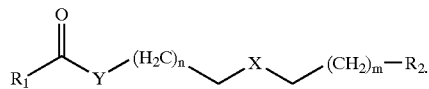

In the above structure, X is a diradical selected from the group represented by the following structures:

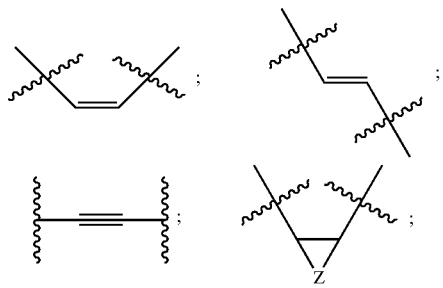

In the above structures, Z is a radical selected from the group consisting of: —$CH_2$ and O; Y is a diradical selected from the group consisting of: —$CH_2$—, —CH($CH_3$)—, —C($CH_3$)$_2$—, —O—, —NH—, —CH(SH)—, —CHSAc)—, —CH(OH)—, —CHCl—, —C(=O)—, —C(=O)CH$_2$—, —CH$_2$NHC(=O)—, and —CH$_2$N(CH$_3$)C(=O)—; R$_1$ is a radical selected from the group consisting of: hydrogen, —NH$_2$, OH, MeNH—, Me$_2$N—, EtNH—, Et$_2$N—, CH$_2$=CHCH$_2$NH—, n-propyl-NH—, i-propyl-NH—, cyclopropyl-NH—, i-propyl-NMe-, butyl-NH—, pyrrolidine-, phenyl-NH—, phenyl(CH$_2$)3NH—, HONH—, MeONMe-, NH$_2$NH—, CH$_3$O—, CH$_3$CH$_2$O—, CH$_3$(CH$_2$)$_2$O—, Me$_2$CHCH$_2$O—, H—, CF$_3$—, BrCH$_2$—, ClCH$_2$—, N$_2$CH—, HOCH$_2$CH$_2$NH—, (HOCH$_2$CH$_2$)$_2$N—, HOCH$_2$CH$_2$CH$_2$NH—, HOCH$_2$CH(OAc)CH$_2$O—, and HO$_2$CCH$_2$NH—; R$_2$ is a radical selected from the group consisting of: —CH$_3$, —CH$_2$OCH$_3$, and —CO$_2$H; and is an integer from 0 to 15; m is an integer from 0 to 15 with the requirement that the sum of n+m is an integer from 11 to 15.

Another aspect of the invention is directed to a method for selectively enhancing a serotonergic signal transduction response of a cell having serotonin receptor subtype 5-HT$_{1A}$. Enhancement is achieved by contacting the cell, in the presence of serotonin, with a quantity of the above serotonergic agent possessing 5-HT$_{1A}$ agonist activity sufficient to selectively enhance the serotonergic signal transduction response of said cell.

Another aspect of the invention is directed to a method for selectively potentiating a cell having a serotonin receptor subtype 5-HT$_{2A}$. The method employs the step of contacting the cell having the serotonin receptor subtype 5-HT$_{1A}$ with a quantity of a serotonergic agent possessing 5-HT$_{2A}$ agonist activity sufficient to selectively potentiate such cell. Preferred serotonergic agents include compounds represented by the structure:

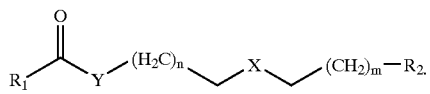

In the above structure, X is a diradical selected from the group represented by the following structures:

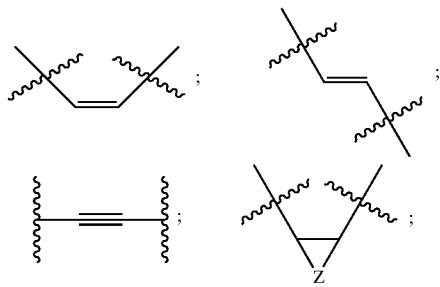

In the above structures, Z is —CH$_2$—; Y is a diradical selected from the group consisting of: —CH$_2$—, —CH(CH$_3$)—, —O—, —CHCl—, —CH$_2$NHC(=O)—, and —CH$_2$N(CH$_3$)C(=O)—; R$_1$ is a radical selected from the group consisting of: hydrogen, —NH$_2$, OH, MeNH—, Me$_2$N—, EtNH—, Et$_2$N—, CH$_2$=CHCH$_2$NH—, HONH—, MeONMe-, NH$_2$NH—, CF$_3$—, and ClCH$_2$—; R$_2$ is a radical selected from the group consisting of: —CH$_3$ and —CH$_2$OH; and n is an integer from 0 to 15; m is an integer from 0 to 15 with the requirement that the sum of n+m is an integer from 11 to 15. However, the following provisos apply: if Y is CH$_2$, X is an ethene diradical, R$_1$ is —NH$_2$, and R$_2$ is —CH$_3$, then n cannot be 1 if m is 12; n cannot be 2 if m is 9; n cannot be 4 if m is 9; n cannot be 5 if m is 2, 4, 6, 8, 10 and 12; n cannot be 6 if m is 6; n cannot be 7 if m is 6; and n cannot be 8 if m is 3.

Another aspect of the invention is directed to a method for selectively enhancing a serotonergic signal transduction response of a cell having serotonin receptor subtype 5-HT$_{2A}$. Enhancement is achieved by contacting the cell, in the presence of serotonin, with a quantity of the above serotonergic agent possessing 5-HT$_{2A}$ agonist activity sufficient to selectively enhance the serotonergic signal transduction response of said cell.

Another aspect of the invention is directed to a method for selectively inhibiting a serotonergic signal transduction response of a cell having serotonin receptor subtype 5-HT$_{1A}$. Inhibition is achieved by contacting the cell with an inhibitory concentration of a serotonergic agent possessing 5-HT$_{1A}$ antagonist activity. Preferred serotonergic agents having antagonist activity include compounds represented by the structure:

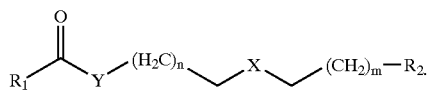

In the above structure, X is an ethene diradical; Y is a methylene diradical; R$_1$ is a radical selected from the group consisting of —NH$_2$ and cyclopropyl-NH—; and R$_2$ is a radical selected from the group consisting of —CH$_3$, —CH$_2$OH and —CONH$_2$. "n" is an integer from 0 to 15; and "m" is an integer from 0 to 15 with the requirement that the sum of n+m is an integer from 11 to 15. However, there are two provisos, viz., if R$_1$ is —NH$_2$, then R$_2$ is not —CH$_3$; and if R$_2$ is —CH$_3$, then R$_1$ is not —NH$_2$.

Another aspect of the invention is directed to a method for selectively inhibiting a serotonergic signal transduction response of a cell having serotonin receptor subtype 5-HT$_{2A}$. Inhibition is achieved by contacting the cell with an inhibitory concentration of a serotonergic agent possessing 5-HT$_{2A}$ antagonist activity. Preferred serotonergic agents having antagonist activity include compounds represented by the structure:

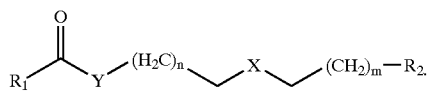

In the above structure, X is an ethene diradical; Y is a diradical selected from the group consisting of: —CH$_2$—, —C(CH$_3$)$_2$—, —NH—, —CH(SH)—, —CH(SAc)—, —CH$_2$NHC(=O)—, and —CH$_2$N(CH$_3$)C(=O)—; R$_1$ is a radical selected from the group consisting of: —NH$_2$, —OH, cyclopropyl-NH—, butyl-NH—, phenyl-NH—, CH$_3$O—, CH$_3$CH$_2$O—, N$_2$CH—, and HOCH$_2$CH(OAc)CH$_2$O—; and R$_2$ is a radical selected from the group consisting of: —CH$_3$, —(CH$_2$)$_2$CH$_3$, —(CH$_2$)$_4$CH$_3$, and —(CH$_2$)$_6$CH$_3$. "n" is an integer from 0 to 15; and "m" is an integer from 0 to 15 with the requirement that the sum of n+m is an integer from 11 to 15. However, there are two provisos, viz., if R$_1$ is —NH$_2$, then Y is not —CH$_2$—; and if Y is —CH$_2$—, then R$_1$ is not —NH$_2$.

Another aspect of the invention is directed to a method for selectively potentiating a cell having a serotonin receptor subtype 5-HT$_{1A}$, Selective potentiation is achieved by contacting the cell having the serotonin receptor subtype 5-HT$_{1A}$ with a quantity of a serotonergic agent possessing 5-HT$_{1A}$ agonist activity sufficient to selectively potentiate said cell. Preferred serotonergic agents having selective potentiating activity include linoleamide and a compound represented by one of the following structures:

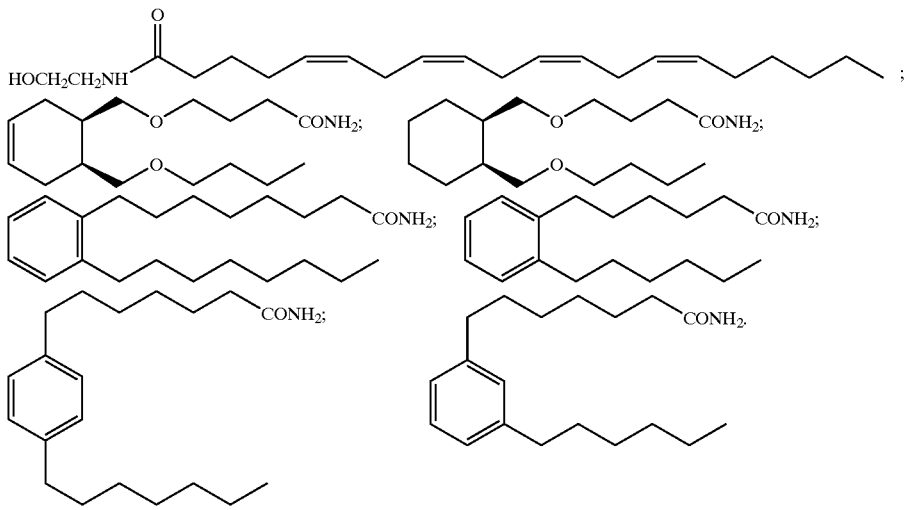

The serotonergic signal transduction response of a cell having serotonin receptor subtype 5-$HT_{1A}$, may also be enhance by contacting the cells with a quantity of the above indicated agents sufficient to enhance the serotonergic signal transduction response.

Another aspect of the invention is directed to a method for selectively potentiating a cell having a serotonin receptor subtype 5-$HT_{2A}$. Selective potentiation is achieved by contacting the cell having the serotonin receptor subtype 5-$HT_{2A}$ with a quantity of a serotonergic agent possessing 5-$HT_{2A}$ agonist activity sufficient to selectively potentiate said cell. Preferred serotonergic agents having selective potentiating activity include a fatty acid primary amide group consisting of $18:2^{9,12}$, $20:2^{11,14}$, $18:3^{6,9,12}$, $18:3^{9,12,15}$, $20:3^{8,11,14}$, $20:3^{11,14,17}$, $20:5^{5,8,11,14,17}$, and $22:6^{4,7,10,13,16,19}$. The serotonergic signal transduction response of a cell having serotorin receptor subtype 5-$HT_{2A}$, may also be enhance by contacting the cells with a quantity of the above indicated agents sufficient to enhance the serotonergic signal transduction response.

DESCRIPTION OF FIGURES

FIG. 3 tabulates the relative % potentiation of fatty acid primary amides against 5-$HT_{2A}$ and 5-$HT_{1A}$.

FIG. 4 tabulates the relative % potentiation of analogs with different carboxamide termini against 5-$HT_{2A}$ and 5-$HT_1A$.

FIG. 5 tabulates the relative % potentiation of analogs with different carboxamide termini against 5-$HT_{2A}$ and 5-$HT_{1A}$.

FIG. 6 tabulates the relative % potentiation of ethanolamide based analogs against 5-$HT_{2A}$ and 5-$HT_{1A}$.

FIG. 11 tabulates (A) the relative % response of potentiation against varying 5-$HT_{1A}$ concentration to oleamide concentration; (B) the relative % response of potentiation against varying 5-$HT_{2A}$ concentration to oleamide concentration.

DETAILED DESCRIPTION OF THE INVENTION

Figure 1:
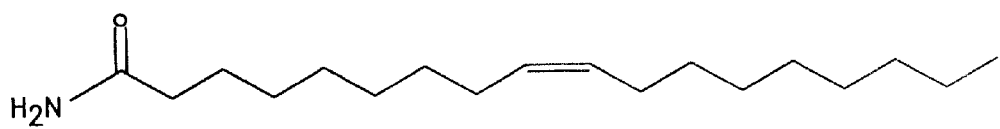
FIG. 1 illustrates oleamide (cis-9-ocatadecenamide, $18:1^9$)

The following examples disclose a set of analogs that potentiate both 5-$HT_{2A}$, and 5-$HT_{1A}$, receptor responses. Some of the analogs inhibit rather than potentiate the 5-$HT_{2A}$, but not 5-$HT_{1A}$, receptor response suggesting such agents may permit selective modulation of serotonin receptor subtypes or even have opposing effects on the different subtypes. These analogs provide information which defines features of oleamide required for potentiation of the 5-$HT_{2A}$ receptor response and report the analogous but more tolerant potentiation of the 5-$HT_{1A}$ receptor which has not been previously examined.

Oleamide is an endogenous fatty acid primary amide which possesses sleep-inducing properties in animals and has been shown to effect serotonergic receptor responses and block gap junction communication. Herein, the potentiation of the 5-$HT_{1A}$ receptor response is disclosed and a study of the structural features of oleamide required for potentiation of the 5-$HT_{2A}$ and 5-$HT_{1A}$ response to serotonin (5-HT) is described. Of the naturally occurring fatty acids, the primary amide of oleic acid (oleamide) is the most effective at potentiating the 5-$HT_{2A}$ receptor response. The structural features required for activity were found to be highly selective. The presence, position, and stereochemistry of the $^9$ cis double bond is required and even subtle structural variations reduce or eliminate activity. Secondary or tertiary amides may replace the primary amide but follow a well-defined relationship requiring small amide substituents suggesting that the carboxamide serves as a hydrogen bond acceptor but not donor. Alternative modifications at the carboxamide as well as modifications of the methyl terminus or the hydrocarbon region spanning the carboxamide and double bond typically eliminate activity.

A less extensive study of the 5-$HT_{1A}$ potentiation revealed that it is more tolerant and accommodates a wider range of structural modifications. An interesting set of analogs was identified that inhibits rather than potentiates the 5-HT$_{2A}$, but not the 5-HT$_{1A}$, receptor response further suggesting that such analogs may permit the selective modulation of serotonin receptor subtypes and even have opposing effects on the different subtypes.

The effects of oleamide and its analogs on rat 5-HT$_{2A}$ and human 5-HT$_{1A}$ receptors were examined using R-SAT transfected cellular assays linked to a colorimetric -galactosidase assay (Messier et al. (1995) *Pharmacol. Toxicol.* 76, 308–311; Brann et al. (1996) *J. Biomol. Screening* 1, 43–45; Brauner-Osborne et al. (1996) *Eur. J. Pharm.* 295, 78–102) which provide results identical to those derived from second messenger assays. Activation of the 5-HT$_{2A}$ or 5-HT$_{1A}$ receptors in 5-HT dependent cell lines results in cell prolification measured by the levels of -galactosidase produced. Analogous to the findings of Huidobro-Toro and Harris (Huidobro-Toro et al. (1996) *Proc. Natl. Acad. Sci. USA* 93, 8078–8082.), treatment with oleamide alone had no effect, but its coadministration with 5-HT provided a significant potentiation of the effect of 5-HT administration alone.

Figure 2:
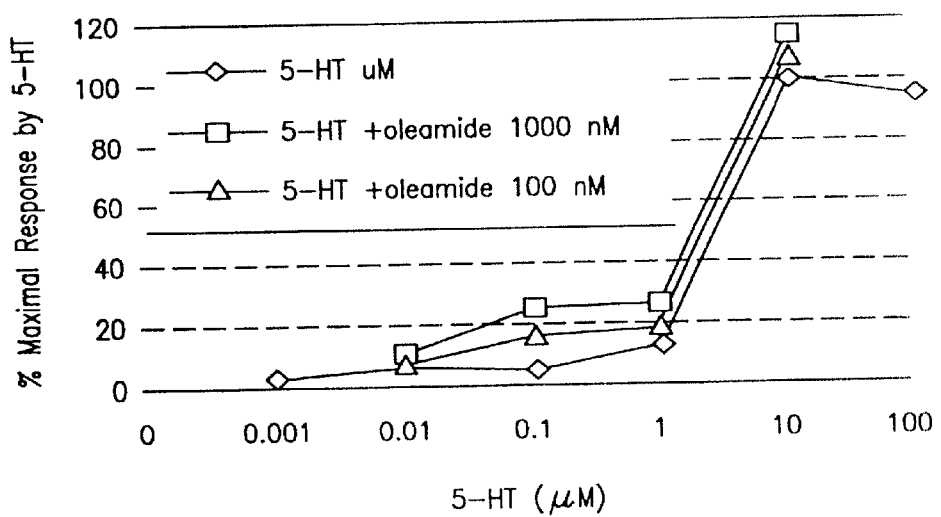
FIG. 2 shows the potentiation of the human 5-$HT_{1A}$ receptor response observed in R-SAT assays in RAT-1 cells transfected with the receptor and linked to a colormetric β-galactosidase assay.

A maximal response with the rat 5-HT$_{2A}$ receptor was observed at 100 nM oleamide when assayed at 100 nM or 1 $\mu$M 5-HT, the concentrations at which the potentiation response (165 and 170%, respectively) was greatest. At higher concentrations of oleamide (1 $\mu$M), no additional potentiation was observed with the rat 5-HT$_{2A}$ receptor (FIG. 11A). Similarly, the maximal potentiation for human 5-HT$_{1A}$ was observed at 100 nM 5-HT (FIG. 2) and concentrations as low as 1–10 nM oleamide produced a measurable effect (FIG. 11B). The maximum effect was observed at concentrations of 100 nM 5-HT and oleamide treatment provided a 370% (100 nM oleamide) or 560% (1 $\mu$M oleamide) potentiation approximating the magnitude observed with the 5-HT$_{2C}$ receptor.

An extensive series of agents was tested at 500 nM for their ability to potentiate the rat 5-HT$_{2A}$ or human 5-HT$_{1A}$ receptor response to 100 nM 5-HT. This spans the concentration range (100 nM-1 $\mu$M) in which oleamide exhibits its greatest potentiation and employs a 5-HT concentration at which the effect was found to be largest. The concentrations employed in the examples below are well within physiologically relevant concentrations. Serotonin levels in human CSF (3.3 ng/ml), plasma (3.4 ng/ml), and platelets (748 ng/10$^9$ platelets) translate into 10–20 nM concentrations (Kumar et al. (1990) *Life Sciences* 47, 1751–1759) which could be much higher at the synapse, and oleamide levels in human plasma (31.7 $\mu$g/mL, 110 $\mu$M) (Arafat et al. (1989) *Life Sci.* 45, 1679–1687) and mouse neuroblastoma N$_{18}$TG$_2$ cells (1.5 $\mu$g/10$^9$ cells, ca. 100× the concentration of anandamide) typically exceed those examined (Bisogno et al. (1997) *Biochem. Biophys. Res. Commun.* 239, 473–479). There was no additional effect when the FAAH enzyme inhibitor PMSF was included in the assay suggesting that the agents susceptible to protease degradation are stable in the assay. The analog screening was conducted with the rat 5-HT$_{2A}$ assay and a subset of analogs was also examined in the human 5-HT$_{1A}$ assay. The results reported are normalized to a 100% potentiation by oleamide for the ease of direct comparisons.

EXAMPLE 1

Potentiation With Fatty Acid Primary Amide Analogs

The first series examined was the primary amides (Wakamatsu et al. (1990) *Biochem. Biophys. Res. Commun.* 168, 423–429; Jain et al. (1992) *J. Med. Chem.* 35, 3584–3586) of the naturally occurring fatty acids and related synthetic analogs (FIGS. 3–4). From these studies, important trends in structural requirements of the endogenous agent emerge. The most effective primary amide of the naturally occurring fatty acids was oleamide. In the 5-HT$_{2A}$ assay and for agents that contain one double bond, the presence, position, and stereochemistry of the olefin as well as the chain length were found to have a pronounced effect.

Removal of the $^9$ double bond (18:0) or its replacement with a trans double bond (18:1$^{9\text{-}trans}$) resulted in no observable potentiation. Shortening the chain length to 14 or 16 carbons resulted in the loss of activity providing weak inhibitors while lengthening the chain substantially diminished the effectiveness. A $^9$ cis olefin exhibited the strongest effect and the potency sharply declined as its position was moved in either direction. This is especially clear in the oleamide series (18:1) where the potency sharply declined as the distance from the $^9$ position increased. Although this is central to oleamide's structure and potentially represents a relationship with either the carboxamide or methyl terminus, the inactivity of the primary amides of 20:1$^9$, 22:1$^9$, and 24:1$^9$ and the modest activity of 20:1$^{13}$, 22:1$^{13}$, and 24:1$^{15}$ suggest that it may be the $^9$ relationship with the methyl terminus that may be most important. Moreover, while extending the distance between the carboxamide and the double bond resulted in reduced or inactive compounds, shortening the length typically provided agents that displayed progressively more potent inhibition versus potentiation. Although the significance of this is not yet clear, it suggests the possibility that tightly regulated endogenous agents may serve to both potentiate or inhibit a serotonin receptor response (FIGS. 3–4).

With the polyunsaturated fatty acid primary amides, those containing two cis double bonds exhibited modest activity and those containing 3–6 double bonds were typically less active. The exception to this generalization is - linolenamide (18:3$^{6,9,12}$) which proved to be a more effective but still less potent agent. Arachidonamide containing four cis double bonds was ineffective.

The behavior of 18:0, 18:1$^{9\text{-}trans}$, 18:1$^8$, 18:1$^{12}$ and 18:2$^{9,12}$ proved analogous to the observations detailed by Huidobro-Toro and Harris et al. (1996) *Proc. Natl. Acad. Sci. USA* 93, 8078–8082 in studies with the 5-HT$_{2C}$ receptor. These similar observations not only indicate that the R-SAT assay for assessment of the 5-HT$_{2A}$ receptor potentiation provides observations analogous to second messenger assays, but also implies that the oleamide structural features required for activity may be well conserved throughout the 5-HT$_2$ receptor subtypes.

In contrast, the 5-HT$_{1A}$ receptor was found to be more tolerant of structural changes. Like the effects at the 5-HT$_{2A}$ receptor, the saturated or trans fatty acid primary amides 18:0 and 18:1$^{9\text{-}trans}$ as well as 18:1$^8$ were less effective than oleamide, albeit not inactive, on the 5-HT$_{1A}$ receptor. Similarly, 14:1$^9$, 16:1$^9$, and linoleamide (18:2$^{9,12}$) were more effective on the 5-HT$_{1A}$ receptor than 5-HT$_{2A}$ with the latter two approaching the potency of oleamide.

EXAMPLE 2

Potentiation With Carboxamide Terminus Analogs

A study of the carboxamide terminus revealed well-defined structural requirements. Not only was the primary amide of oleic acid capable of potentiating the 5-HT response, but secondary and tertiary amides also provided a comparable potentiation provided the amide substituents were small (FIGS. 4–5). The activity smoothly progresses through the series with the maximum effect observed with the NMe$_2$ tertiary amide. As the amide substituents further increased in size, the effect diminished and ultimately provided inactive derivatives. Thus, the primary carboxamide is not required although its efficacy approximates that of the most potent amide. This suggests that the carboxamide may serve as a H-bond acceptor but need not serve as a H-bond donor. In addition, the cyclopropyl amide was uniquely effective at inhibiting the response to serotonin at the 5-HT$_{2A}$ receptor. Although endogenous agents that may act similarly have not been identified, such allosteric inhibitors at 5-HT$_{2A}$ may prove to be useful biochemical tools and potentially interesting therapeutics.

In contrast to the well defined effects on the 5-HT$_{2A}$ receptor, both the isopropyl and cyclopropyl amides as well as the methyl amide were found to be effective at potentiating 5-HT$_{1A}$ even though the first two were inactive or inhibitory on 5-HT$_{2A}$. Such distinctions suggest that derivatives of oleamide may be developed that not only possess greater potentiation effects, but that can also selectively modulate the various serotonin receptor subtypes or even have opposing effects (i.e., cyclopropyl amide).

Alternative substitutions for the carboxamide including oleic acid itself, oleyl esters, alcohols, amines, aldehydes, acetals, and electrophilic ketones did not provide a comparable potentiation of 5-HT$_{2A}$ but appear to be better tolerated with 5-HT$_1$A (FIGS. 4–5). Of particular interest are oleyl aldehyde and the trifluoromethyl ketone (FIG. 5, R=H and CF$_3$). Both not only possess polarized carbonyls and can serve as H-bond acceptors, but both are potent inhibitors of FAAH which is responsible for the degradation of oleamide (Patterson et al. (1996) *J. Am. Chem. Soc.* 118, 5938–5945). This dual activity suggests that they may not only potentiate the activity of oleamide by inhibiting its degradation, but that they may also serve as oleamide agonists at the 5-HT1A receptor.

EXAMPLE 3

Potentiation With Oleyl Ethanolamide, Anandamide and Related Analogs

An important subset of modified carboxamides is the ethanolamide derivatives (Bachur et al. (1965) *J. Biol. Chem.* 240, 1019–1024; Ramachandran et al. (1992) *Biochem. Arch.* 8, 369–377; Schmid et al. (1990) *Prog. Lipid Res.* 29, 1–43; Hanus et al. (1993) *J. Med. Chem.* 36, 3032–3034) which include anandamide. Consequently, the ethanolamides and bis-(ethanol)amides of oleic and arachidonic acid were examined (FIG. 6). Both derivatives of oleic acid were inactive providing no effect on the 5-HT$_{2A}$ receptor while those of arachidonic acid including anandamide were weakly inhibitory. Similarly, recent studies have implicated 2-arachidonyl glycerol as an endogenous ligand for the cannabinoid receptor (Mechoulam et al. (1995) *Biochem. Pharmacol.* 50, 83–90) and diacylglycerols including 1-oleyl-2-acetylglycerol have been reported as inhibitors of Chinese hamster V79 cell gap junctions (Aylsworth et al. (1986) *Cancer Res.* 46, 4527–4533). This latter compound was examined and it did not potentiate, but rather weakly inhibited the 5-HT$_{2A}$ receptor response.

Both oleyl ethanolamide and anandamide were found to potentiate the 5-HT$_{1A}$ receptor response to 5-HT and the former was more potent. Although this might be interpreted to suggest a special significance for the ethanolamides, oleyl propanolamide was equally effective. As such, the results are more consistent with the simpler interpretation that the 5-HT$_{1A}$ receptor potentiation is more tolerant of modifications in the carboxamide terminus and accommodates a wider range of secondary or tertiary amides (FIG. 6).

EXAMPLE 4

Potentiation With Putative Precursors and Related Analogs

Figure 7:
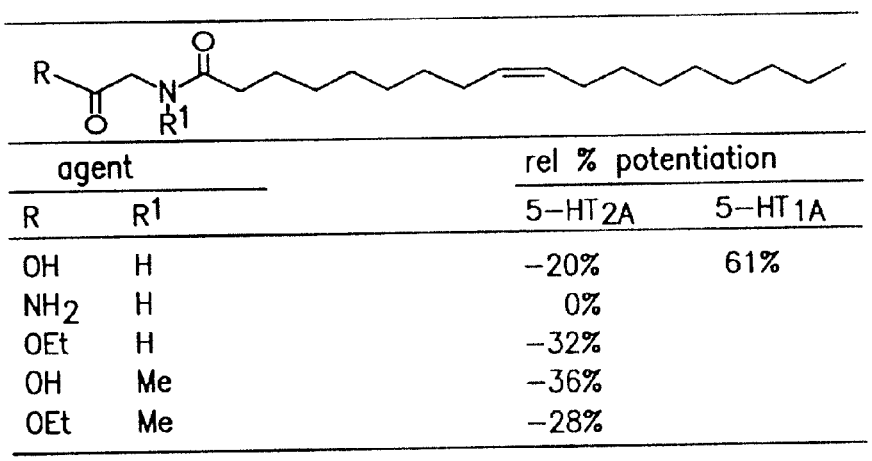
FIG. 7 tabulates the relative % potentiation of N-Oleyl glycine derivatives against 5-$HT_{2A}$ and 5-$HT_{1A}$.

The potential that oleamide may be stored as a N-oleyl glycinamide derivative and released upon -hydroxylation of glycine by a peptidylglycine -amidating monoxygenase (Merkler et al. (1996) *Arch. Biochem. Biophys.* 330, 430–434) led to the examination of a set of N-oleyl glycine derivatives (FIG. 7). None of the derivatives potentiated the 5-HT$_{2A}$ serotonin receptor response and most proved to be weak inhibitors. This is consistent with their behavior as large secondary or tertiary amide derivatives and their activity follows the prior trends (FIGS. 4–6). In contrast, N-oleyl glycine was a weak potentiator of the 5-HT$_{1A}$ receptor consistent with its more tolerant accommodation of modifications in the carboxamide terminus.

EXAMPLE 5

Potentiation With Methyl Terminus Analogs

Figure 8:
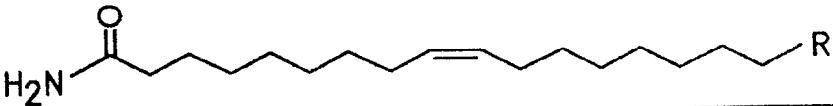
FIG. 8 tabulates the relative % potentiation of analogs with varying methyl termini against 5-$HT_{2A}$ and 5-$HT_{1A}$.

The potentiation of 5-HT$_{2A}$ or 5-HT$_{1A}$ was especially sensitive to the structural characteristics at the methyl terminus (FIG. 8). Extending the length of the methyl terminus chain and the incorporation of polar functional groups resulted in a loss of activity.

EXAMPLE 6

Potentiation With Analogs Which Have Modifications in the Double Bond

Figure 9:
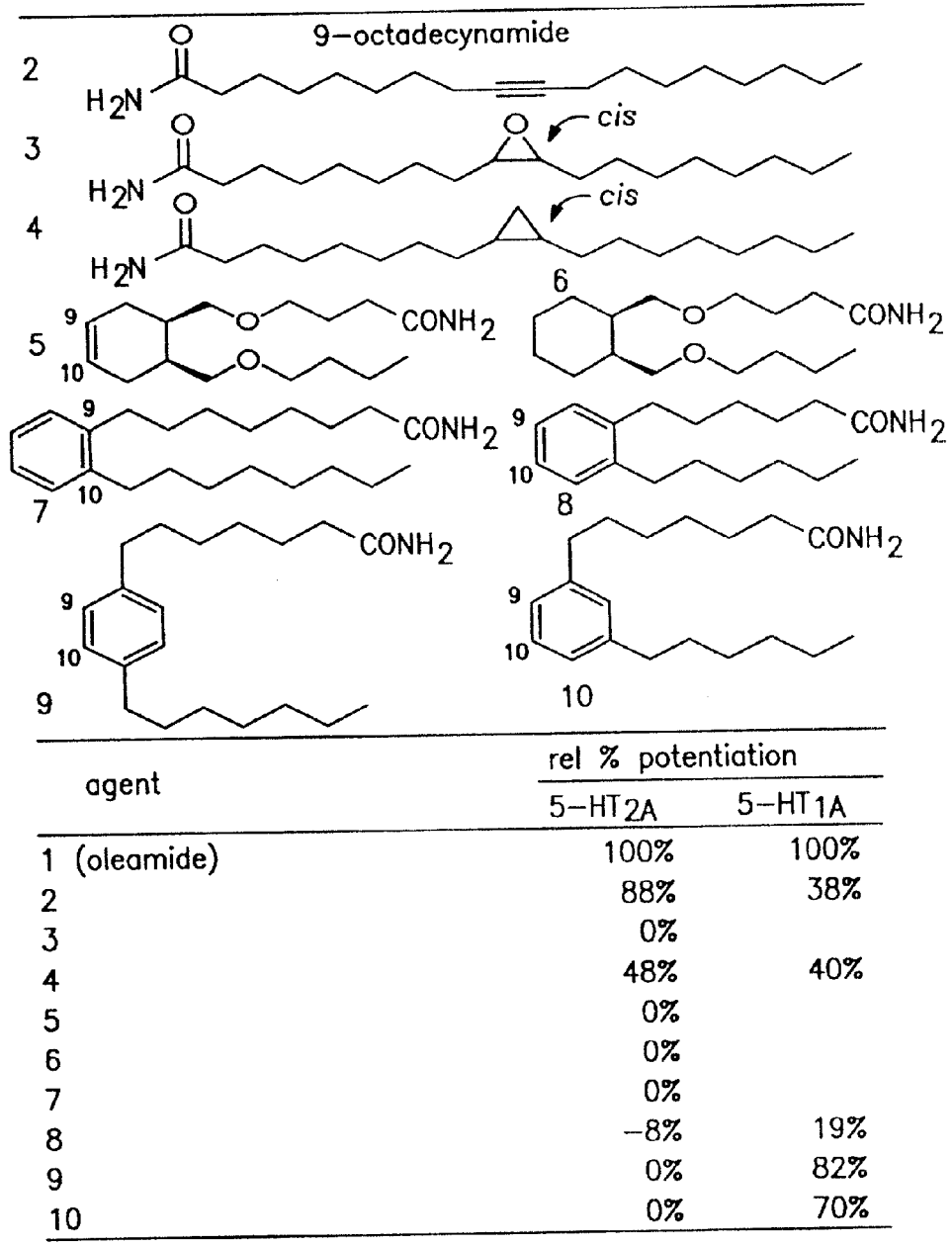
FIG. 9 tabulates the relative % potentiation of analogs with olefin modifications and substitutions against 5-$HT_2$, and 5-$HT_{1A}$.

The agents 2–10 were examined to define the role of the olefin (FIG. 9). Analogous to the observations made with octadecanamide (18:0) and the trans-9-octadecenamide (18:1$^{9\text{-}trans}$) which were ineffective at potentiating 5-HT$_{2A}$, nearly all agents were ineffective. These include 7–10 for which a benzene ring was incorporated into the structure at a location that mimics the $^9$ double bond as well as 5 and 6 which mimic a hairpin conformation. Although it is difficult to draw specific conclusions from their inactivity, it highlights that the effects of oleamide at the 5-HT$_{2A}$ receptor are surprisingly selective for the endogenous lipid. The exceptions include 9-octadecynamide (2) which was nearly equipotent with oleamide and 4 which was approximately 50% as effective. The observation that the former is so effective suggests that the appropriate presentation of a -system in addition to the conformational effects of the cis double bond may be important. Consistent with this, 4 versus 3 proved surprisingly effective and may benefit from the partial characteristics of the cyclopropane which would allow it to mimic both and conformational characteristics of the cis double bond.

Similar observations with the 5-HT$_{1A}$ receptor were made with 2 and 4. In contrast to the 5-HT$_{2A}$ results, both 9 and 10, but not 8, were effective at potentiating the 5-HT$_{1A}$ receptor response and imply that an extended versus hairpin conformation of oleamide might be important at the 5-HT$_{1A}$ receptor.

EXAMPLE 7

Potentiation With Analogs Which Have Modifications in the Linking Chain

Figure 10:
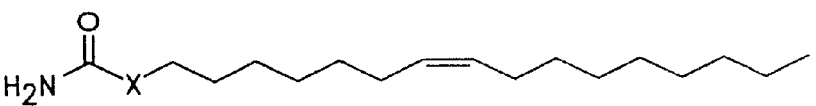
FIG. 10 tabulates the relative % potentiation of analogs with linker modifications and substitutions against 5-$HT_{2A}$ and 5-$HT_{1A}$.

Modifications in the seven carbon chain linking the olefin and carboxamide were examined and found to have a detrimental effect with 5-HT$_{2A}$ (FIG. 10). Substitution of the -carbon or its replacement with a heteroatom resulted in a loss of activity or provided agents that inhibited the 5-HT$_{2A}$ response. Most notable are 2,2-dimethyloleamide as well as the urethane (X=NH) which proved to be potent inhibitors.

In contrast, most of the linking chain modifications did not adversely affect the 5-HT$_{1A}$ potentiation and this is significant in several respects. It is consistent with the greater tolerance for carboxamide modifications observed at the 5-HT$_{1A}$ receptor and highlights again that many oleamide analogs may have distinguishing effects on the serotonin receptor subtypes. Moreover, the first seven entries in FIG. 10 constitute analogs that are more resistant to hydrolytic FAAH degradation and suggest an improved duration of effect would accompany their enhanced efficacy in vivo. In addition, the two -keto amide (X=CO, COCH$_2$) in FIG. 10 are potent inhibitors of FAAH illustrating that they may serve to potentiate the effects of oleamide by inhibiting its hydrolysis and serve as oleamide agonists in their own right at the 5-HT$_{1A}$ receptor.

EXAMPLE 8

General Synthetic Conditions for the Preparation of Oleamide Based Analogs

The fatty acid primary amides (FIG. 3) were prepared by treating the acid chlorides, generated from the corresponding carboxylic acid and oxalyl chloride, with aqueous NH$_4$OH according the procedures in Cravatt et al. (1996) *J. Am. Chem. Soc.* 118, 580–590; Patterson et al. (1996) *J. Am. Chem. Soc.* 118, 5938–5945). Many of the fatty acids were commercially available (Sigma, Aldrich, Fluka), and the remainder were synthesized as detailed vida infra.

Most agents in FIGS. 4–5 were prepared by condensing oleoyl chloride with the appropriate amine or alcohol following procedures in Cravatt et al. (1996) *J. Am. Chem. Soc.* 118, 580–590; Patterson et al. (1996) *J. Am. Chem. Soc.* 118, 5938–5945; Roe et al. *J. Am. Chem. Soc.* 71, 2215–2218; Roe et al. (1952) *J. Am. Chem. Soc.* 74, 3442–3443. The remaining agents in FIGS. 4–5 are commercially available (Sigma, Pfaltz & Bauer) or are prepared vida infra.

The ethanolamides (FIG. 6) were similarly prepared or purchased (Pfaltz & Bauer). The synthesis of the 18-hydroxyoleamide was described in Cravatt et al. (1996) *J. Am. Chem. Soc.* 118, 580–590 and standard transformations following protocols detailed therein were used to prepare the remaining agents in FIG. 8.

N-Oleoyl glycine (FIG. 7) was prepared by coupling glycine ethyl ester to oleic acid with EDCI (Cravatt et al. (1996) *J. Am. Chem. Soc.* 118, 580–590; Patterson et al. (1996) *J. Am. Chem. Soc.* 118, 5938–5945) followed by sequential transformation to the carboxylic acid (LiOH) and glycinamide (EDCI, NH4OH;). N-Oleoyl sarcosine was purchased (Pfaltz and Bauer) and converted to its ethyl ester by coupling with EtOH (DCC).

The agents in FIG. 9 were prepared as described in Cravatt et al. (1996) *J. Am. Chem. Soc.* 118, 580–590; Simmons et al. (1959) *J. Am. Chem. Soc.* 81, 4256–4264) or by a series of Wittig couplings to the appropriately substituted o, m, or p-cyanobenzaldehyde. Substitutions at the α-carbon (FIG. 10) were installed by treating the enolate of oleic acid or methyl oleate (generated by LDA) with an appropriate electrophile as previously detailed in Patterson et al. (1996) *J. Am. Chem. Soc.* 118, 5938–5945). The primary carbamate and urethanes were prepared from the corresponding alcohols or amines (HCl, NaOCN).

EXAMPLE 9

Discussion and Conclusions

The above examples illustrate that the structural features of oleamide required for potentiation of the 5-HT$_{2A}$ receptor response are well-defined supporting a selective site of action. Of the naturally occurring fatty acids, oleamide is the most effective and other endogenous fatty acid amides including arachidonamide, anandamide, and oleyl ethanolamide were less active or ineffective. For oleamide, the presence, position, and stereochemistry of $^9$ cis double bond is required and even subtle structural variations reduce or eliminate activity. Secondary or tertiary amides but not acids, esters, aldehydes, alcohols, amines, acetals, or electrophilic or polarized ketones may replace the primary carboxamide. Even the amide substitutions follow a well-defined relationship limited to small amide substituents. Modifications of the methyl terminus or in the hydrocarbon chain linking the carboxamide and cis double bond typically eliminate the activity. In contrast, the 5-HT$_{1A}$ receptor was more tolerant of structural modifications especially at the carboxamide terminus.

The well-defined structural features of oleamide required for potentiation of the 5-HT$_{2A}$ or 5-HT$_{1A}$ receptor response in the presence of serotonin provides the opportunity to correlate the properties with physiological states including sleep (Lerner, R. A. (1997) *Proc. Natl. Acad. Sci. USA* 94, 13375–13377). Such studies will clarify whether the serotonergic effects of oleamide and related agents may be responsible. Many of the well-defined structural features of oleamide are tightly conserved among the 5-HT$_{2A}$, 5-HT$_{1A}$, and 5-HT$_{2C}$ receptors suggesting they may be well conserved throughout the 5-HT$_1$ and 5-HT$_2$ receptor subtypes. However, distinguishing structural effects were observed where the 5-HT$_{1A}$ receptor was more tolerant of structural modifications in the carboxamide terminus of oleamide.

In addition, several agents including a small set of naturally occurring fatty acid primary amides were identified that inhibited rather than potentiated the 5-HT$_{2A}$ but not 5-HT$_{1A}$ receptor response. Although the significance of these observations is not yet clear, it not only suggests the possibility that tightly regulated endogenous agents may serve to both potentiate or inhibit a serotonin response, but that analogs of oleamide may permit the selective modulation of serotonin receptor subtypes and, in selected instances, even have opposing effects on the different receptor subtypes.

The studies to date have demonstrated that at concentrations of 100 nM serotonin, 100 nM oleamide potentiates 5-HT$_{2C}$ (365%, 11), 5-HT$_{1A}$ (370%, results herein) and 5-HT$_{2A}$ receptors (165% for results herein, 228% (Thomas et al. (1997) *Proc. Natl. Acad. Sci. USA* 94, 14115–14119) and 260% (Huidobro-Toro et al. (1996) *Proc. Natl. Acad. Sci. USA* 93, 8078–8082), inhibits 5-HT, receptors (−50%, Thomas et al. (1997) *Proc. Natl. Acad. Sci. USA* 94, 14115–14119), and has no effect on the ion gated channel 5-HT$_3$ receptor. The identification of such agents provide new biochemical tools for the study of serotonin receptors and may lead to therapeutic applications involving selective modulation of the serotonin response at the receptor subtypes.

While a preferred form of the invention has been shown in the drawings and described, since variations in the preferred form will be apparent to those skilled in the art, the invention should not be construed as limited to the specific form shown and described, but instead is as set forth in the following claims.

EXPERIMENTAL PROTOCOLS

General $^1$H and $^{13}$C nmr spectra were recorded either on a Bruker AM-250, a Bruker AMX-400 or a Bruker AMX-500 spectrometer. Residual protic solvent CHCl$_3$ ($\delta_H$=7.26 ppm, $\delta_C$=77.0), d$_4$-methanol ($\delta_H$=3.30 ppm, $\delta_C$=49.0) and D$_2$O ($\delta_H$=4.80 ppm, $\delta_C$ (of CH$_3$CN)=1.7 ppm) or TMS ($\delta_H$=0.00 ppm) were used as internal reference. Coupling constants were measured in Hertz (Hz). HRMS were recorded using FAB method in a m-nitrobenzylalcohol (NBA) matrix doped with NaI or CsI. Infra-red spectra were recorded on a Perkin-Elmer FTIR 1620 spectrometer. Enantiomeric excess was determined by HPLC using a Daicel Chemical Industries CHIRALPAK AD column. Optical rotations were measured with an Optical Activity AA-1000 polarimeter. Melting points were taken on a Thomas Hoover capillary melting point apparatus and are uncorrected. Column chromatography was performed on Merck Kieselgel 60 (230–400 mesh). Analytical thin layer chromatography was performed using pre-coated glass-backed plates (Merck Kieselgel F$_{254}$) and visualized by cerium molybdophosphate or ninhydrin. Diethyl ether, tetrahydrofuran (THF) and toluene (PhCH$_3$) were distilled from sodium-benzophenone ketyl, dichloromethane (DCM) and acetonitrile from calcium hydride. Other solvents and reagents were purified by standard procedures if necessary.

Materials. The analogs examined were purchased (Sigma, Pfaltz & Bauer, Aldrich), prepared as described or synthesized following protocols previously detailed (Cravatt et al. (1996) *J. Am. Chem. Soc.* 118, 580–590; Patterson et al. (1996) *J. Am. Chem. Soc.* 118, 5938–5945; Roe et al. (1952) *J. Am. Chem. Soc.* 74, 3442–3443; Patterson, J. E. (1997, November) Chemical and Structural Studies on Analogs of Oleamide, an Endogenous Sleep-inducing Lipid, Ph.D. Thesis, The Scripps Research Institute, La Jolla, Calif.).

Methods. The assays were conducted with R-SAT kits (Receptor Technologies Inc, Winooski, Vt.) containing NIH 3T3 cells expressing the rat 5-HT$_{2A}$ receptor (Suter et al. (1987) *Fundam. Appl. Toxicol.* 9, 785–794; Pritchett et al. (1988) *EMBO J* 7, 4135–4140) or RAT-1 cells expressing the human 5-HT$_{1A}$ receptor (Lam et al. (1996) *Biochem. Biophys. Res. Commun.* 219, 853–858; Kobilka et al. (1987) *Nature* 329, 75–79) cotransfected with the -galactosidase gene and were performed according to the procedures provided (Messier et al. (1995) *Pharmacol. Toxicol.* 76, 308–311; Brann et al. (1996) *J. Biomol. Screening* 1, 43–45). The cells in Dulbecco modified Eagle's medium containing serotonin (100 nM) and the analogs (500 nM) were incubated in a humidified 5% CO$_2$ incubator at 37° C. for 4 or 5 days for the 5-HT$_{2A}$ and 5-HT$_{1A}$ transfected cells, respectively. Levels of -galactosidase were measured after incubation with the chromogenic substrate o-nitrophenyl- -D-galactopyranoside (20) at 30° C. in a humidified incubator for a recommended period of time and the absorbance was measured at 405 nm. The results were normalized to 100% for oleamide (rel. % potentiation) for the ease of comparison and are the average of 2–8 determinations.

18:0 (stearamide) as illustrated in FIG. 3: purchased from Aldrich and recrystallized once before use.

General procedure for the preparation of fatty amides (compounds disclosed in FIG. 3): The fatty acid (1 equiv) was dissolved in dry CH$_2$Cl$_2$ (0.2 M) and cooled to 0° C. under a N$_2$ atmosphere. Oxalyl chloride (2M in CH$_2$Cl$_2$, 3 equiv) was added slowly. The solution was warmed to 25° C. and allowed to stir for 3 h in the dark. The solvent was removed in vacuo and the flask cooled to 0° C. Excess concentrated NH$_4$OH was added slowly and the crude product was purified by chromatography on SiO$_2$ using EtOAc/hexanes as an eluent. Fatty acids were purchased from Sigma unless otherwise indicated.

14:1$^9$(Myristoleamide) as illustrated in FIG. 3 Synthesized exactly as found in the general procedure vida supra; all starting reagents were purchased from Aldrich, Acros, or Sigma and resulting white solid was purified by chromatography (50%–100% EtOAc/hexanes, gradient elution) to afford 94% desired product: mp 76–78° C.; $^1$H NMR (CD$_3$OD, 400 MHz) δ 5.29–5.22 (m, 2H), 2.11 (t, 2H, J=7.6 Hz), 1.95 (m, 4H), 1.52 (p, 2H, J=7.3 Hz, 1.25 (m, 12H), 0.83 (m, 3H); $^{13}$C NMR (CD$_3$OD, 100 MHz) δ 179.3, 130.82, 130.77, 36.6, 33.1, 30.8, 30.5, 30.3, 30.2, 28.1, 27.9, 26.9, 23.4, 14.4; IR (NaCl, film) $\upsilon_{max}$ 3324, 2923, 2852, 2523, 2466, 2355, 1630, 1526, 1469, 1435, 1410, 1095, 956, 755, 723 cm$^{-1}$; HRFABMS m/z (M+H$^+$) 226.2164 (requires m/z 226.2171).

16:1$^9$(Palmitoleamide) as illustrated in FIG. 3 Synthesized exactly as found in the general procedure vida supra; all starting reagents were purchased from Aldrich, Acros, or Sigma and resulting white solid was purified by chromatography (50% EtOAc/hexanes) to afford 96% desired product: mp 74–75° C.; $^1$H NMR (CD30D, 400 MHz) δ 5.30–5.22 (m, 2H), 2.11 (t, 2H, J=7.6 Hz), 1.94 (m, 4H), 1.53 (p, 2H, J=7.1 Hz), 1.25 (m, 16H), 0.82 (t, 3H, J=6.8 Hz); $^{13}$C NMR (CD$_3$OD, 100 MHz) δ 179.3, 130.9, 130.8, 36.5, 33.0, 30.8 (2), 30.4, 30.34 (2), 30.27, 30.1, 28.2, 26.8, 23.7, 14.5; IR (NaCl, film) $\upsilon_{max}$ 3324, 3003, 2923, 2852, 2523, 2466, 2357, 1631, 1527, 1469, 1437, 1410, 1215, 758 cm$^{-1}$; HRFABMS m/z (M+Cs$^+$) 386.1448 (requires m/z 386.1460).

17:1$^8$ as illustrated in FIG. 3 Synthesized exactly as found in the general procedure vida supra; all starting reagents were purchased from Aldrich, Acros, or Sigma and resulting white solid was purified by chromatography: white solid: mp 68–69° C.; $^1$H NMR (CDCl$_3$, 400 MHz) δ 5.64 (br, 1H), 5.43 (br, 1H), 5.38–5.26 (m, 2H), 2.19 (t, 2H, J=7.6 Hz), 2.03–1.95 (m, 4H), 1.62 (m, 2H), 1.37–1.24 (m, 18H), 0.85 (t, 3H, J=6.9 Hz); $^{13}$C NMR (CDCl$_3$, 100 MHz) δ 175.6, 130.2, 129.4, 35.9, 31.9, 29.7, 29.5, 29.4, 29.3, 28.8, 27.2, 27.0, 25.4, 22.7, 14.1; IR (film) $\upsilon_{max}$ 3359, 3193, 2922, 2852, 1659, 1633, 1466, 1412, 1136 cm$^{-1}$; FABHRMS (NBA-CsI) m/z 400.1603 (C$_{17}$H$_{33}$NO+Cs$^+$ requires 400.1616). 8Z-heptadecenoic acid prepared as previously described (JACS, 1996, 118, 5938–5945).

18:1$^6$(Petroselinamide) as illustrated in FIG. 3 Synthesized exactly as found in the general procedure vida supra; all starting reagents were purchased from Aldrich, Acros, or Sigma and resulting white solid was purified by chromatography: white solid: mp 73–74° C.; $^1$H NMR (CDCl$_3$, 500 MHz) δ 6.15 (br, 1H), 5.61 (br, 1H), 5.34–5.27 (m, 2H), 2.17 (t, 2H, J=7.5 Hz), 2.01 (q, 2H, J=7.0 Hz), 1.96 (q, 2H, J=7.0 Hz), 1.60 (p, 2H, J=7.8 Hz), 1.35 (p, 2H, J=7.8 Hz), 1.28–1.21 (m, 18H), 0.83 (t, 3H, J=7.0 Hz); $^{13}$C NMR (CDCl$_3$, 125 MHz) δ 175.9, 130.4, 129.0, 35.8, 31.9, 29.7, 29.62, 29.59, 29.5, 29.3, 29.2, 27.2, 26.8, 25.1, 22.6, 14.1; IR (film) $\upsilon_{max}$ 3366, 3203, 3000, 2917, 2848, 1647, 1465, 1415, 734 cm$^{-1}$; FABHRMS (NBA-CsI) m/z 282.2810 (C$_{18}$H$_{35}$NO+H$^+$ requires 282.2797).

18:1$^7$ as illustrated in FIG. 3 Synthesized exactly as found in the general procedure vida supra; all starting reagents were purchased from Aldrich, Acros, or Sigma and resulting white solid was purified by chromatography: white solid: mp 70–71° C.; $^1$H NMR (CDCl$_3$, 400 MHz) δ 6.26 (br, 1H), 5.67 (br, 1H), 5.34–5.24 (m, 2H), 2.16 (t, 2H, J=7.6 Hz), 2.00–1.92 (m, 4H), 1.58 (p, 2H, J=7.5 Hz), 1.31–1.21 (m, 20H), 0.83 (t, 3H, J=6.8 Hz); $^{13}$C NMR (CDCl$_3$, 100 MHz) δ 176.1, 130.1, 129.3, 35.9, 31.8, 29.7, 29.6 (2), 29.5, 29.4, 29.3, 29.2, 28.8, 27.1, 27.0, 25.4, 22.6, 14.0; IR (film) $υ_{max}$ 3392, 3179, 3013, 2920, 2848, 1647, 1468, 1416, 1312, 1115, 806, 719, 628 cm$^{-1}$; FABHRMS (NBA-NaI) m/z 282.2801 (C$_{18}$H$_{35}$NO+H$^+$ requires 282.2797).

18:1$^8$ as illustrated in FIG. 3 Synthesized exactly as found in the general procedure vida supra; all starting reagents were purchased from Aldrich, Acros, or Sigma and resulting white solid was purified by chromatography or prepared as previously described exactly (JACS, 1996, 118, 580–590).

18:1$^9$(Oleamide) as illustrated in FIG. 3: Prepared as previously described exactly (JACS, 1996, 118, 580–590).

18:1$^{9\text{-}trans}$(Elaidamide) as illustrated in FIG. 3: Prepared as previously described. (JACS, 1996, 118, 580–590).

18:1$^{11}$(Vaccenamide) as illustrated in FIG. 3: Prepared as previously described. (JACS, 1996, 118, 580–590).

18:1$^{12}$ as illustrated in FIG. 3 Synthesized exactly as found in the general procedure vida supra; all starting reagents were purchased from Aldrich, Acros, or Sigma and resulting white solid was purified by chromatography: white solid: mp 77–78° C.; $^1$H NMR (CDCl$_3$, 500 MHz) δ 6.11 (br, 1H), 5.62 (br, 1H), 5.34–5.26 (m, 2H), 2.16 (t, 2H, J=7.5 Hz), 1.97 (q, 4H, J=6.0 Hz), 1.58 (p, 2H, J=7.3 Hz), 1.32–1.22 (m, 20H), 0.84 (t, 3H, J=7.0 Hz); $^{13}$C NMR (CDCl$_3$, 125 MHz) δ 176.1, 129.84, 129.78, 35.9, 31.5, 29.7, 29.51, 29.46, 29.42, 29.38, 29.3, 29.23, 29.18, 27.1, 25.5, 22.5, 14.0; IR (film) $υ_{max}$ 3356, 3188, 2917, 2848, 1727, 1661, 1633, 1469, 1410, 1135, 700, 628 cm$^{-1}$; FABHRMS (NBA-CsI) m/z 282.2810 (C$_{18}$H$_{35}$NO+H$^+$ requires 282.2797).

18:1$^{13}$ as illustrated in FIG. 3 Synthesized exactly as found in the general procedure vida supra; all starting reagents were purchased from Aldrich, Acros, or Sigma and resulting white solid was purified by chromatography: white solid: mp 86–87° C.; $^1$H NMR (CDCl$_3$, 400 MHz) δ 6.03 (br, 1H), 5.57 (br, 1H), 5.34–5.27 (m, 2H), 2.17 (t, 2H, J=7.6 Hz), 1.98 (m, 4H), 1.58 (p, 2H, J=7.2 Hz), 1.30–1.22 (m, 20H), 0.86 (t, 3H, J=7.0 Hz); $^{13}$C NMR (CDCl$_3$, 100 MHz) δ 176.0, 129.82, 129.78, 35.9, 31.9, 29.7, 29.55 (2), 29.48, 29.4, 29.3, 29.24, 29.19, 27.2, 26.8, 25.5, 22.3, 13.9; IR (film) $υ_{max}$ 3357, 3192, 3003, 2917, 2848, 1656, 1632, 1470, 1422, 1410, 1136, 721, 636 cm$^{-1}$; FABHRMS (NBA-NaI) m/z 304.2608 (C$_{18}$H$_{35}$NO+Na$^+$ requires 304.2616).

18:1$^{15}$ as illustrated in FIG. 3 Synthesized exactly as found in the general procedure vida supra; all starting reagents were purchased from Aldrich, Acros, or Sigma and resulting white solid was purified by chromatography: white solid: mp 92–93° C.; $^1$H NMR (CDCl$_3$, 500 MHz) δ 5.70 (br, 1H), 5.46 (br, 1H), 5.35–5.27 (m, 2H), 2.19 (t, 2H, J=7.5 Hz), 1.99 (h, 4H, J=6.8 Hz), 1.60 (p, 2H, J=7.3 Hz), 1.31–1.22 (m, 20H), 0.92 (t, 3H, J=7.5 Hz); $^{13}$C NMR (CDCl$_3$, 125 MHz) δ 175.7, 131.5, 129.3, 35.9, 29.7, 29.60, 29.56, 29.5, 29.4, 29.31, 29.26, 29.2, 27.1, 25.5, 20.5, 14.4; IR (film) $υ_{max}$ 3356, 3189, 2918, 2848, 1659, 1632, 1470, 1420, 1410, 1137 cm$^{-1}$; FABHRMS (NBA-CsI) m/z 282.2707 (C$_{18}$H$_{35}$NO+H$^+$ requires 282.2797).

19:1$^{10}$ as illustrated in FIG. 3 Synthesized exactly as found in the general procedure vida supra; all starting reagents were purchased from Aldrich, Acros, or Sigma and resulting white solid was purified by chromatography: white solid: mp 71–72° C.; $^1$H NMR (CDCl$_3$, 400 MHz) δ 5.95 (br, 1H), 5.53 (br, 1H), 5.35–5.26 (m, 2H), 2.17 (t, 2H, J=7.6 Hz), 1.97 (m, 4H), 1.59 (p, 2H, J=7.2 Hz), 1.25–1.23 (m, 22H), 0.84 (t, 3H, J=6.9 Hz); $^{13}$C NMR (CDCl$_3$, 100 MHz) δ 176.0, 129.9, 129.7, 35.9, 31.9, 29.7, 29.5, 29.34, 29.27, 29.2, 27.2, 25.5, 22.6, 14.1; IR (film) $υ_{max}$ 3362, 3194, 2920, 2850, 1651, 1633, 1469, 1422 cm$^{-1}$; FABHRMS (NBA-CsI) m/z 296.2961 (C$_{19}$H$_{37}$NO+H$^+$ requires 296.2953). 10Z-nonadecenoic acid prepared as previously described (JACS, 1996, 118, 5938–5945).

20:1$^5$ as illustrated in FIG. 3 Synthesized exactly as found in the general procedure vida supra; all starting reagents were purchased from Aldrich, Acros, or Sigma and resulting white solid was purified by chromatography: (50%–100% EtOAc/hexanes, gradient elution) to afford 86% desired product; mp 82° C.; $^1$H NMR (CD$_3$OD, 400 MHz) δ 5.35–5.23 (m, 2H), 2.11 (t, 2H, J=7.6 Hz), 2.02–1.93 (m, 4H), 1.56 (p, 2H, J=7.5 Hz), 1.28–1.15 (m, 24H), 0.81 (t, 3H, J=6.9 Hz); $^{13}$C NMR (CDCl$_3$, 100 MHz) δ 175.5, 131.2, 128.4, 35.2, 31.9, 29.7, 29.7, 29.67, 29.63, 29.3, 27.3, 26.5, 25.4, 22.7, 14.1; IR (NaCl, film) $υ_{max}$ 3371, 2917, 2849, 2535, 2361, 1632, 1511, 1471, 1423 cm$^{-1}$; HRFABMS m/z (M+H$^+$) 310.3100 (requires m/z 310.3110)

20:1$^8$ as illustrated in FIG. 3 Synthesized exactly as found in the general procedure vida supra; all starting reagents were purchased from Aldrich, Acros, or Sigma and resulting white solid was purified by chromatography: white solid: mp 71–72° C.; $^1$H NMR (CDCl$_3$, 500 MHz) δ 5.70 (br, 1H), 5.44 (br, 1H), 5.36–5.27 (m, 2H), 2.19 (t, 2H, J=7.5 Hz), 1.99–1.96 (m, 4H), 1.61 (p, 2H, J=7.0 Hz), 1.30–1.23 (m, 24H), 0.85 (t, 3H, J=7.0 Hz); $^{13}$C NMR (CDCl$_3$, 125 MHz) δ 175.7, 130.1, 129.6, 35.9, 31.9, 29.73, 29.66, 29.62, 29.54, 29.33, 29.31, 29.1, 29.0, 27.2, 27.1, 25.5, 22.7, 14.1; IR (film) $υ_{max}$ 3389, 3200, 3003, 2917, 2848, 1645, 1467, 1418, 722 cm$^{-1}$; FABHRMS (NBA-NaI) m/z 310.3125 (C$_{20}$H$_{39}$NO+H$^+$ requires 310.3110).

20:1$^9$ as illustrated in FIG. 3 Synthesized exactly as found in the general procedure vida supra; all starting reagents were purchased from Aldrich, Acros, or Sigma and resulting white solid was purified by chromatography: The crude product was chromatographed (SiO$_2$, 1×10 cm, 50–100% EtOAc/hexanes, gradient elution) to afford 9 (21.4 mg, 61%) as a white solid: mp 72–73° C.; $^1$H NMR (CDCl$_3$, 400 MHz) δ 5.56 (br, 1H), 5.41 (br, 1H), 5.36–5.27 (m, 2H), 2.19 (t, 2H, J=7.6 Hz), 1.99–1.96 (m, 4H), 1.61 (p, 2H, J=7.1 Hz), 1.28–1.23 (m, 28H), 0.85 (t, 3H, J=6.8 Hz); $^{13}$C NMR (CDCl$_3$, 100 MHz) δ 175.6, 130.0, 129.7, 35.9, 31.9, 29.75, 29.67, 29.64, 29.55, 29.34, 29.31, 29.22, 29.19, 29.10, 27.2, 27.1, 25.5, 22.7, 14.1; IR (film) $υ_{max}$ 3390, 3199, 2917, 2848, 1643, 1467, 722 cm$^{-1}$; FABHRMS (NBA-NaI) m/z 338.3416 (C$_{22}$H$_{43}$NO+H$^+$ requires 338.3423). Acid prepared in a manner analogous to 22:1$^9$.

20:1$^{11}$ as illustrated in FIG. 3 Synthesized exactly as found in the general procedure vida supra; all starting reagents were purchased from Aldrich, Acros, or Sigma and resulting white solid was purified by chromatography: White solid was purified by chromatography (50%–66% EtOAc/hexanes, gradient elution) to afford 97% desired product; mp 81–82° C.; $^1$H NMR (CD$_3$OD, 400 MHz) δ 5.29–5.21 (m, 2H), 2.10 (t, 2H, J=7.6 Hz), 1.93 (m, 4H), 1.51 (p, 2H, J=7.3 Hz), 1.22 (m, 24H), 0.83 (t, 3H, J=6.9 Hz); $^{13}$C NMR (CD$_3$OD, 100 MHz) δ 179.3, 130.8 (2), 36.6, 33.1, 30.88, 30.86, 30.6, 30.5, 30.4, 28.2, 28.1, 26.9, 23.8, 14.5; IR (NaCl, film) $υ_{max}$ 3324, 2918, 2849, 2522, 2353, 1629, 1527, 1468, 1437, 1410, 955, 721 cm$^{-1}$; HRFABMS m/z (M+Cs$^+$) 442.2068 (requires 442.2086).

20:1$^{13}$ as illustrated in FIG. 3 Synthesized exactly as found in the general procedure vida supra; all starting reagents were purchased from Aldrich, Acros, or Sigma and resulting white solid was purified by chromatography: White solid was purified by chromatography (33% EtOAc/ hexanes) to afford 89% desired product; mp 84–85° C.; $^1$H NMR (CD$_3$OD, 400 MHz) δ 5.29–5.21 (m, 2H), 2.10 (t, 2H, J=7.6 Hz), 1.93 (m, 4H), 1.51 (p, 2H, J=7.2 Hz), 1.21 (m, 24H), 0.81 (t, 3H, J=6.9 Hz); $^{13}$C NMR (CD$_3$OD, 100 MHz) δ 179.3, 130.9 (2), 36.6, 33.0, 30.9 (2), 30.8 (2), 30.7 (2), 30.5, 30.3 (2), 30.1, 28.2, 28.1, 26.9, 23.8, 14.5; IR (NaCl, film) υ$_{max}$ 3324, 2917, 2849, 2523, 2347, 1630, 1526, 1470, 1430, 1410, 953, 721 cm$^{-1}$; HRFABMS m/z (M+H$^+$) 310.3099 (requires m/z 310.3110).

22:1$^9$ as illustrated in FIG. 3 7-bromoheptanol was protected (TBDPSCl, Et$_3$N, DMAP) and treated with PPh$_3$ to generate a phosphonium salt (284.9 mg, 0.42 mmol, 1 eq) that was dissolved in anhydrous THF (2.6 mL) under Ar at −78° C. was treated dropwise with KHMDS (0.5M in toluene, 0.85 mL, 0.43 mmol, 1 eq). The orange solution was allowed to stir for 40 min at −78° C. before tridecanal (100 μL, 0.42 mmol, 1 eq) was added. The reaction was warmed to 25° C. and allowed to stir 1 h before saturated aqueous NH$_4$Cl (30 mL) was added. The aqueous layer was extraced with EtOAc (3×30 mL). The organic layers were dried (Na$_2$SO$_4$), filtered, and concentrated in vacuo. The crude product was chromatographed (SiO$_2$, 2×8 cm, 0–5% EtOAc/hexanes, gradient elution) to afford alkene (131.0 mg, 55%) as a clear oil; $^1$H NMR (CDCl$_3$, 500 MHz) δ 7.69 (dd, 4H, J=8.0, 1.5 Hz), 7.44–7.37 (m, 6H), 5.40–5.34 (m, 2H), 3.67 (t, 2H, J=6.5 Hz), 2.03 (q, 4H, J=6.0 Hz), 1.58 (p, 2H, J=7.5 Hz), 1.35–1.28 (m, 30H), 1.07 (s, 9H), 0.90 (t, 3H, J=7.0 Hz); $^{13}$C NMR (CDCl$_3$, 125 MHz) δ 135.6, 134.2, 129.90, 129.86, 129.5, 127.5, 64.0, 32.6, 31.9, 29.8, 29.70, 29.67, 29.6, 29.5, 29.4, 29.33, 29.26, 27.2, 26.9, 25.8, 22.7, 19.2, 14.1; IR (film) υ$_{max}$ 2925, 2854, 1472, 1457, 1112, 823, 701, 608 cm$^{-1}$; FABHRMS (NBA-CsI) m/z 695.3649 (C$_{38}$H$_{62}$OSi+Cs$^+$ requires 695.3624).

A solution of alkene (128.2 mg, 0.23 mmol, 1 eq) in THF (2.2 mL) under N$_2$ was treated with TBAF (1M in THF, 0.46 mL, 0.46 mmol, 2 eq) and stirred at 25° C. for 2.5 h. Water (30 mL) was added and the aqueous layers were extracted with EtOAc (3×30 mL). The organic layers were dried (Na$_2$SO$_4$), filtered, and concentrated in vacuo. The crude product was chromatographed (SiO$_2$, 2×5 cm, 5–33% EtOAc/hexanes, gradient elution) to afford alcohol (51.2 mg, 69%) as a white film; $^1$H NMR (CDCl$_3$, 400 MHz) δ 5.36–5.29 (m, 2H), 3.62 (t, 2H, J=6.6 Hz), 2.02–1.97 (m, 4H), 1.54 (p, 2H, J=6.8 Hz), 1.28–1.24 (m, 30H), 0.86 (t, 3H, J=6.8 Hz); $^{13}$C NMR (CDCl$_3$, 100 MHz) δ 129.9, 129.8, 63.1, 32.8, 31.9, 29.73, 29.67, 29.64, 29.6, 29.5, 29.39, 29.35, 29.31, 29.2, 27.2, 25.7, 22.7, 14.1; IR (film) υ$_{max}$ 3328, 2923, 2852, 1457, 1055 cm$^{-1}$; FABHRMS (NBA-NaI) m/z 325.3475 (C$_{22}$H$_{44}$O+H$^+$ requires 325.3470).

A solution of alcohol (48.5 mg, 0.15 mmol, 1 eq) in anhydrous DMF (1 mL) under N$_2$ was treated with PDC (0.28 g, 0.74 mmol, 5 eq) and stirred at 25° C. for 3.5 h. The reaction mixture was filtered through celite and the filtrate was concentrated in vacuo. The crude product was chromatographed (SiO$_2$, 1×8 cm, 10–20% EtOAc/hexanes, gradient elution) to afford acid (36.2 mg, 72%) as a clear oil; $^1$H NMR (CDCl$_3$, 400 MHz) δ 5.37–5.28 (m, 2H), 2.33 (t, 2H, J=7.5 Hz), 2.01–1.97 (m, 4H), 1.61 (p, 2H, J=7.2 Hz), 1.29–1.24 (m, 28H), 0.86 (t, 3H, J=6.8 Hz); $^{13}$C NMR (CDCl$_3$, 100 MHz) δ 179.9, 130.0, 129.7, 34.0, 31.9, 29.8, 29.7, 29.6, 29.4, 29.3, 29.14, 29.06, 29.03, 27.2, 27.1, 24.7, 22.7, 14.1; IR (film) υ$_{max}$ 2918, 2850, 1689, 1466, 1411, 1297, 918, 722, 687 cm$^{-1}$; FABHRMS (NBA-NaI) m/z 361.3091 (C$_{22}$H$_{42}$O$_2$+Na$^+$ requires 361.3083).

A solution of acid (34.9 mg, 0.103 mmol, 1 eq) in anhydrous CH$_2$Cl$_2$ (0.5 mL) under N$_2$ at 0° C. was treated with oxalyl chloride (2M in CH$_2$Cl$_2$, 0.13 mL, 0.26 mmol, 3 eq). The reaction mixture was warmed to 25° C. and stirred for 3 h before the solvent was removed in vacuo. The residue was cooled to 0° C. and treated with excess concentrated NH$_4$OH (1 mL). Water (30 mL) was added and the aqueous layer was extracted with EtOAc (3×30 mL). The organic layers were dried (Na$_2$SO$_4$), filtered, and concentrated in vacuo. The crude product was chromatographed (SiO$_2$, 1×10 cm, 50–100% EtOAc/hexanes, gradient elution) to afford 22:1$^9$ (21.4 mg, 61%) as a white solid: mp 72–73° C.; $^1$H NMR (CDCl$_3$, 400 MHz) δ 5.56 (br, 1H), 5.41 (br, 1H), 5.36–5.27 (m, 2H), 2.19 (t, 2H, J=7.6 Hz), 1.99–1.96 (m, 4H), 1.61 (p, 2H, J=7.1 Hz), 1.28–1.23 (m, 28H), 0.85 (t, 3H, J=6.8 Hz); $^{13}$C NMR (CDCl$_3$, 100 MHz) δ 175.6, 130.0, 129.7, 35.9, 31.9, 29.75, 29.67, 29.64, 29.55, 29.34, 29.31, 29.22, 29.19, 29.10, 27.2, 27.1, 25.5, 22.7, 14.1; IR (film) υ$_{max}$ 3390, 3199, 2917, 2848, 1643, 1467, 722 cm$^{-1}$; FAB-HRMS (NBA-NaI) m/z 338.3416 (C$_{22}$H$_{43}$NO+H$^+$ requires 338.3423).

22:1$^{13}$(Erucamide) as illustrated in FIG. 3 Synthesized exactly as found in the general procedure vida supra; all starting reagents were purchased from Aldrich, Acros, or Sigma and resulting white solid was purified by chromatography: White solid was purified by chromatography (50% EtOAc/hexanes) to afford 96% desired product; mp 83–84° C.; $^1$H NMR (CDCl$_3$, 400 MHz) δ 5.29–5.21 (m, 2H), 2.09 (t, 2H, J=7.6 Hz), 1.93 (m, 4H), 1.51 (p, 2H, J=7.3 Hz), 1.20 (m, 28H), 0.81 (t, 3H, J=6.9 Hz); $^{13}$C NMR (CDCl$_3$, 100 MHz) δ 175.8, 129.88, 129.85, 36.0, 31.9, 29.7, 29.58, 29.53, 29.50, 29.46, 29.32, 29.29, 29.18, 27.2, 25.3, 22.7, 14.1; IR (NaCl, film) υ$_{max}$ 3375, 2920, 2847, 2544, 1633, 1511, 1468, 1417, 932, 721 cm$^{-1}$; HRFABMS m/z (M+Cs$^+$) 470.2413 (requires m/z 470.2399).

24:1$^9$ as illustrated in FIG. 3 Synthesized exactly as found in the general procedure vida supra; all starting reagents were purchased from Aldrich, Acros, or Sigma and resulting white solid was purified by chromatography: (SiO$_2$, 1×10 cm, 50–100% EtOAc/hexanes, gradient elution) to afford 13 (20.7 mg, 67%) as a white solid: mp 74–75° C.; $^1$H NMR (CDCl$_3$, 500 MHz) δ 5.49 (br, 1H), 5.39 (br, 1H), 5.35–5.28 (m, 2H), 2.19 (t, 2H, J=7.8 Hz), 2.00–1.96 (m, 4H), 1.61 (p, 2H, J=7.0 Hz), 1.29–1.23 (m, 32H), 0.85 (t, 3H, J=7.0 Hz); $^{13}$C NMR (CDCl$_3$, 125 MHz) δ 175.5, 130.0, 129.7, 35.9, 31.9, 29.8, 29.68, 29.65, 29.56, 29.3, 29.23, 29.19, 29.1, 27.21, 27.15, 25.5, 22.7, 14.1; IR (film) υ$_{max}$ 3389, 3184, 2917, 2848, 1044, 1467, 1416, 1119 cm$^{-1}$; FABHRMS (NBA-NaI) m/z 366.3740 (C$_{24}$H$_{47}$NO+H$^+$ requires 366.3736). Acid prepared in a manner analogous to 22:1$^9$.

24:1$^{15}$(Nervonamide) as illustrated in FIG. 3 Synthesized exactly as found in the general procedure vida supra; all starting reagents were purchased from Aldrich, Acros, or Sigma and resulting white solid was purified by chromatography: White solid was purified by chromatography (33%–66% EtOAc/hexanes, gradient elution) to afford 91% desired product; mp 87–88° C.; $^1$H NMR (CDCl$_3$, 400 MHz) δ 5.36–5.28 (m, 2H), 2.19 (t, 2H, J=7.6 Hz), 1.98 (m, 4H), 1.60 (p, 2H, J=7.2 Hz), 1.36–1.23 (m, 32H), 0.85 (t, 3H, J=6.8 Hz); $^{13}$C NMR (CDCl$_3$, 100 MHz) δ 175.7, 129.9 (2), 35.94, 35.91, 31.9, 29.8, 29.63, 29.56, 29.54, 29.50, 29.46, 29.33, 29.30, 29.22, 27.18, 25.5, 22.7, 14.1; IR (NaCl, film) υ$_{max}$ 3392, 2919, 2847, 2543, 2358, 1633, 1468, 1412, 720 cm$^{-1}$; HRFABMS m/z (M+H$^+$) 366.3727 (requires m/z 366.3736).

18:2$^{9,12}$(Linoleamide) as illustrated in FIG. 3: Prepared as previously described. (JACS, 1996, 118, 580–590).

18:2$^{9,12\text{-}trans}$(Linoelaidarnide) as illustrated in FIG. 3 Synthesized exactly as found in the general procedure vida supra; all starting reagents were purchased from Aldrich, Acros, or Sigma and resulting white solid was purified by chromatography: (50% EtOAc/hexanes) to afford 88% desired product; mp 83–84° C.; $^1$H NMR (CD$_3$OD, 400 MHz) δ 5.35–5.24 (m, 4H), 2.59 (m, 2H), 2.10 (t, 2H, J=7.6 Hz), 1.90 (m, 4H), 1.51 (p, 2H, J=7.2 Hz), 1.33–1.13 (m, 14H), 0.81 (t, 3H, J=7.0 Hz); $^{13}$C NMR (CD$_3$OD, 100 MHz) δ 179.3, 131.99, 131.92, 130.0, 129.9, 36.6, 36.5, 33.6 (2), 32.5, 30.7, 30.4, 30.3 (2), 30.1, 26.9, 23.6, 14.5; IR (NaCl, film) $υ_{max}$ 3371, 2917, 2847, 2540, 2345, 1622, 1470, 1420, 964, 716 cm$^{-1}$; HRFABMS m/z (M+Cs$^+$) 412.1598 (requires m/z 412.1616)

20:2[11,14] as illustrated in FIG. 3 Synthesized exactly as found in the general procedure vida supra; all starting reagents were purchased from Aldrich, Acros, or Sigma and resulting white solid was purified by chromatography: (50%–100% EtOAc/hexanes, gradient elution) to afford 92% desired product; mp 47–49° C.; $^1$H NMR (CD$_3$OD, 400 MHz) δ 5.31–5.20 (m, 4H), 2.67 (t, 2H, J=6.2 Hz), 2.12 (t, 2H, J=7.6 Hz), 1.97 (q, 4H, J=6.8 Hz), 1.52 (p, 2H, J=7.3 Hz), 1.32–1.17 (m, 18H), 0.82 (t, 3H, J=6.9); $^{13}$C NMR (CD$_3$OD, 100 MHz) δ 179.2, 130.9 (2), 129.1 (2), 36.5, 32.7, 30.8 (2), 30.7 (2), 30.5 (2), 30.41, 30.36, 28.2, 26.9, 26.6, 23.7, 14.5; IR (NaCl, film) $υ_{max}$ 3324, 3009, 2919, 2849, 2513, 2466, 2400, 1733, 1634, 1528, 1469, 1410, 1250, 1048, 758 cm$^{-1}$; LRFABMS m/z (M+H$^+$) 308.

18:3[9,12,15]: (α-linolenamide) as illustrated in FIG. 3 Synthesized exactly as found in the general procedure vida supra; all starting reagents were purchased from Aldrich, Acros, or Sigma and resulting yellow gel was purified by chromatography: (33%–100% EtOAc/hexanes, gradient elution) to afford 99% desired product. $^1$H NMR (CD$_3$OD, 400 MHz) δ 5.33–5.18 (m, 6H), 2.76 (t, 4H, J=6.0 Hz), 2.11 (t, 2H, J=7.6 Hz), 2.00 (m, 4H), 1.52 (p, 2H, J=7.1 Hz), 1.26 (m, 8H), 0.89 (t, 3H, J=7.5 Hz); $^{13}$C NMR (CD$_3$OD, 100 MHz) δ 179.2, 132.7, 131.1, 129.2 (2), 128.8, 128.2, 36.5, 30.7, 30.4, 30.31, 30.26, 28.2, 26.9, 26.5, 26.4, 21.5, 14.7; IR (NaCl, film) $υ_{max}$ 3326, 3009, 2924, 2851, 2526, 2356, 1629, 1527, 1469, 1436, 1410, 955, 723 cm$^{-1}$; HRFABMS m/z (M+Cs$^+$) 410.1452 (requires m/z 410.1460).

20:3[8,11,14] as illustrated in FIG. 3 Synthesized exactly as found in the general procedure vida supra; all starting reagents were purchased from Aldrich, Acros, or Sigma and resulting yellow gel was purified by chromatography: (50%–100% EtOAc/hexanes, gradient elution) to afford 78% desired product. $^1$H NMR (CD$_3$OD, 400 MHz) δ 5.32–5.21 (m, 6H), 2.73 (m, 4H), 2.11 (t, 2H, J=7.6 Hz), 1.98 (m, 4H), 1.51 (p, 2H, J=7.2 Hz), 1.34–1.20 (m, 12H), 0.81 (t, 3H, J=6.9 Hz); $^{13}$C NMR (CD$_3$OD, 100 MHz) δ 179.3, 131.1, 131.0, 129.22, 129.16, 128.9, 128.8, 36.5, 32.7 30.7, 30.5, 30.3, 30.1, 28.2 (2), 26.9, 26.6 (2), 23.7, 14.5; IR (NaCl, film) $υ_{max}$ 3328, 3009, 2925, 2852, 2525, 2468, 2402, 1634, 1527, 1466, 1411, 1330, 1202, 959 cm$^{-1}$; HRFABMS m/z (M+Cs$^+$) 438.1756 (requires m/z 438.1773).

20:3[11,14,17] as illustrated in FIG. 3 Synthesized exactly as found in the general procedure vida supra; all starting reagents were purchased from Aldrich, Acros, or Sigma and resulting yellow gel was purified by chromatography: (50%–100% EtOAc/hexanes, gradient elution) to afford 84% desired product. $^1$H NMR (CD$_3$OD, 400 MHz) δ 5.32–5.17 (m, 6H), 2.71 (t, 4H, J=5.9 Hz), 2.10 (t, 2H, J=7.6 Hz), 2.01–1.92 (m, 4H), 1.51 (p, 2H, J=7.3 Hz), 1.29–1.23 (m, 12H), 0.88 (t, 3H, J=7.6 Hz); $^{13}$C NMR (CD$_3$OD, 100 MHz) δ 179.3, 132.7, 131.1, 129.21, 129.17, 128.8, 128.2, 36.5, 30.8, 30.64, 30.62, 30.5, 30.4, 30.3, 28.2, 26.9, 26.5, 26.4, 21.5, 14.7; IR (NaCl, film) $υ_{max}$ 3324, 3010, 2963, 2919, 2849, 2525, 2351, 1627, 1529, 1469, 1439, 1410, 956, 721 cm$^{-1}$; HRFABMS m/z (M+Cs$^+$) 438.1765 (requires m/z 438.1773).

20:4[5,8,11,14] as illustrated in FIG. 3: purchased from Sigma.

20:5[5,8,11,14,17] as illustrated in FIG. 3 Synthesized exactly as found in the general procedure vida supra; all starting reagents were purchased from Aldrich, Acros, or Sigma and clear oil gel was purified by chromatography: $^1$H NMR (CDCl$_3$, 500 MHz) δ 5.38–5.35 (m, 10H), 2.83–2.78 (m, 8H), 2.21 (t, 2H, J=7.5 Hz), 2.11 (q, 2H, J=6.5 Hz), 2.06 (p, 2H, J=7.5 Hz), 1.71 (p, 2H, J=7.5 Hz), 0.95 (t, 3H, J=7.5 Hz); $^{13}$C NMR (CDCl$_3$, 125 MHz) δ 175.1, 132.1, 129.0, 128.9, 128.6, 128.3, 128.19, 128.16, 128.07, 127.8, 35.1, 26.5, 25.6, 25.5, 25.2, 20.6, 14.3; IR (film) $υ_{max}$ 3354, 3192, 3011, 2961, 1660, 1614, 1441, 1410, 1264 cm$^{-1}$; FAB-HRMS (NBA-NaI) m/z 302.2489 (C$_{20}$H$_{31}$NO+H$^+$ requires 302.2484).

22:6[4,7,10,13,16,19] as illustrated in FIG. 3 Synthesized exactly as found in the general procedure vida supra; all starting reagents were purchased from Aldrich, Acros, or Sigma and clear oil gel was purified by chromatography: (50%–100% EtOAc/hexanes, gradient elution) to afford 55% desired product. $^1$H NMR (CD$_3$OD, 400 MHz) δ 5.33–5.17 (m, 12H), 2.80–2.71 (m, 10H), 2.31 (m, 2H), 2.14 (t, 2H, J=7.4 Hz), 1.98 (p, 2H, J=7.4 Hz), 0.87 (t, 3H, J=7.6 Hz); $^{13}$C NMR (CD$_3$OD, 100 MHz) δ 178.4, 132.8, 130.1, 129.4, 129.23, 129.19, 129.16, 129.09, 128.9, 128.2, 36.3, 26.54, 26.49, 26.42, 24.5, 21.5, 14.7; IR (NaCl, film) $υ_{max}$ 3341, 3198, 3012, 2955, 1661, 1393, 1262, 923 cm$^{-1}$; HRFABMS m/z (M+Cs$^+$) 460.1640 (requires m/z 460.1616).

General procedure for the preparation of oleic amide derivatives varying about carboxamide (unless otherwise described) as illustrated in FIG. 4: One equivalent of oleic acid was dissolved in dry CH$_2$Cl$_2$ (0.2 M) and cooled to 0° C. under a N$_2$ atmosphere. Oxalyl chloride (2M in CH$_2$Cl$_2$, 3 equiv) was added slowly. The solution was warmed to 25° C. and allowed to stir for 3 hours in the dark. The solvent was then removed in vacuo and the flask cooled to 0° C. Excess free amine (amines that were available as the hydrochloride salts were extracted into EtOAc from a 50% NaOH solution before use) or alcohols were added slowly. The crude product was purified by chromatography on SiO$_2$ using EtOAc/hexanes as an eluent.

Oleic acid: Agent purchased from Aldrich.

MeNH derivative as illustrated in FIG. 4 Synthesized exactly as found in the general procedure for derivatives varying about carboxamide vida supra; all starting reagents were purchased from Aldrich, Acros, or Sigma: White solid was purified by chromatography (50% EtOAc/hexanes) to afford 95% desired product; mp 34–35° C.; $^1$H NMR (CD$_3$OD, 400 MHz) δ 5.29–5.21 (m, 2H), 2.61 (s, 3H), 2.07 (t, 2H, J=7.6 Hz), 1.93 (m, 4H), 1.50 (p, 2H, J=7.0 Hz), 1.23–1.21 (m, 20H), 0.81 (t, 3H, J=6.9 Hz); $^{13}$C NMR (CD$_3$OD, 100 MHz) δ 176.7, 130.9, 130.8, 37.0, 33.1, 30.87, 30.85, 30.7, 30.5, 30.4, 30.34, 30.27, 28.2, 27.0, 26.3, 23.8, 14.5; IR (NaCl, film) $υ_{max}$ 3301, 3005, 2921, 2853, 2418, 1651, 1557, 1463, 1403, 1164, 723 cm$^{-1}$; HRFABMS m/z (M+H$^+$) 296.2940 (requires m/z 296.2953).

Me$_2$N derivative as illustrated in FIG. 4 Synthesized exactly as found in the general procedure for derivatives varying about carboxamide vida supra; all starting reagents were purchased from Aldrich, Acros, or Sigma: Pale yellow oil was purified by chromatography (33% EtOAc/hexanes) to afford 99% desired product. $^1$H NMR (CD$_3$OD, 400

MHz) δ 5.32–5.24 (m, 2H), 2.99 (s, 3H), 2.86 (s, 3H), 2.29 (t, 2H, J=7.6 Hz), 1.97 (m, 4H), 1.53 (p, 2H, J=7.3 Hz), 1.28–1.24 (m, 20H), 0.85 (t, 3H, J=6.8 Hz); $^{13}$C NMR (CD$_3$OD, 100 MHz) δ 175.4, 130.82 130.77, 37.8, 35.7, 34.2, 33.1, 30.90, 30.87, 30.7, 30.5, 30.4, 30.3, 28.2, 26.3, 23.8, 14.6; IR (NaCl, film) $υ_{max}$ 2923, 2853, 1652, 1463, 1394, 1267, 1141, 723 cm$^{-1}$; HRFABMS m/z (M+H$^+$) 310.3101 (requires m/z 310.3110).

EtNH derivative as illustrated in FIG. 4 Synthesized exactly as found in the general procedure for derivatives varying about carboxamide vida supra; all starting reagents were purchased from Aldrich, Acros, or Sigma: White solid was purified by chromatography (33% EtOAc/hexanes) to afford 99% desired product; mp 34–35° C.; $^1$H NMR (CDCl$_3$, 400 MHz) δ 5.53 (br, 1H), 5.35–5.26 (m, 2H), 3.28–3.21 (m, 2H), 2.11 (t, 2H, J=7.7 Hz), 2.01–1.92 (m, 4H), 1.58 (p, 2H, J=7.4 Hz), 1.30–1.23 (m, 20H), 1.09 (t, 3H, J=7.3 Hz), 0.83 (t, 3H, J=6.9 Hz); $^{13}$C NMR (CDCl$_3$, 100 MHz) δ 173.0, 130.0, 129.7, 36.8, 34.2, 31.9, 29.73, 29.67, 29.5, 29.29 (2), 29.25 (2), 29.1, 27.2, 27.1, 25.8, 22.7, 14.9, 14.1; IR (NaCl, film) $υ_{max}$ 3304, 3084, 2918, 2850, 1641, 1551, 1466, 938, 721 cm$^{-1}$; HRFABMS m/z (M+H$^+$) 310.3099 (requires m/z 310.3110).

Et$_2$N derivative as illustrated in FIG. 4 Synthesized exactly as found in the general procedure for derivatives varying about carboxamide vida supra; all starting reagents were purchased from Aldrich, Acros, or Sigma: Pale orange oil was purified by chromatography (20%–50% EtOAc/hexanes, gradient elution) to afford 99% desired product. $^1$H NMR (CD$_3$OD, 400 MHz) δ 5.32–5.25 (m, 2H), 3.31 (p, 4H, J=7.2 Hz), 2.28 (t, 2H, J=7.6 Hz), 1.97 (m, 4H), 1.55 (p, 2H, J=7.3 Hz), 1.29–1.24 (m, 20H), 1.13 (t, 3H, J=7.1 Hz), 1.04 (t, 3H, J=7.1 Hz), 0.85 (t, 3H, i=6.9 Hz); $^{13}$C NMR (CD$_3$OD, 100 MHz) δ 174.4, 130.81, 130.77, 43.4, 41.4, 33.9, 33.1, 30.91, 30.87, 30.7, 30.5, 30.4, 30.3, 28.3, 26.7, 23.8, 14.7, 14.6, 13.4; IR (NaCl, film) $υ_{max}$ 2925, 2853, 1651, 1462, 1427, 1379, 1309, 1261, 1223, 1139, 1096, 944, 791, 722 cm$^{-1}$; HRFABMS m/z (M+H$^+$) 338.3430 (requires m/z 338.3423).

PrNH derivative as illustrated in FIG. 4 Synthesized exactly as found in the general procedure for derivatives varying about carboxamide vida supra; all starting reagents were purchased from Aldrich, Acros, or Sigma: white solid: mp 28–29° C.; $^1$H NMR (CDCl$_3$, 400 MHz) δ 6.01 (br, 1H), 5.29–5.21 (m, 2H), 3.12 (q, 2H, J=6.8 Hz), 2.08 (t, 2H, J=7.6 Hz), 1.95–1.90 (m, 4H), 1.54 (p, 2H, J=7.4 Hz), 1.43 (s, 2H, J=7.2 Hz), 1.21–1.19 (m, 20H), 0.89–0.78 (m, 6H); $^{13}$C NMR (CDCl$_3$, 100 MHz) δ 173.1, 129.8, 129.6, 41.0, 36.6, 31.7, 29.60, 29.56, 29.4, 29.2 (4), 29.0, 27.04, 27.01, 25.7, 22.7, 22.5, 13.9, 11.2; IR (film) $υ_{max}$ 3298, 2924, 2854, 1648, 1552, 1464, 1378, 1253, 1153, 757 cm$^{-1}$; ESI (M+H$^+$) 324.

i-PrNH derivative as illustrated in FIG. 4 Synthesized exactly as found in the general procedure for derivatives varying about carboxamide vida supra; all starting reagents were purchased from Aldrich, Acros, or Sigma: white solid: mp 25° C.; $^1$H NMR (CDCl$_3$, 400 MHz) δ 5.46–5.45 (br, 1H), 5.33–5.24 (m, 2H), 4.07–3.96 (m, 1H), 2.07 (t, 2H, J=7.6 Hz), 1.97–1.93 (m, 4H), 1.56 (p, 2H, J=7.1 Hz), 1.24–1.15 (m, 20H), 1.08 (d, 6H, J=6.6 Hz), 0.83 (t, 3H, J=6.8 Hz); $^{13}$C NMR (CDCl$_3$, 100 MHz) δ 172.2, 129.9, 129.7, 41.0, 36.9, 31.8, 29.7, 29.6, 29.4, 29.23, 29.19, 29.1, 27.11, 27.08, 25.7, 22.7, 22.6, 14.0; IR (film) $υ_{max}$ 3291, 2925, 2854, 1645, 1558, 1540, 1457, 1174, 1130, 722 cm$^{-1}$; FABHRMS (NBA-NaI) m/z 324.3259 (C$_{23}$H$_{41}$)NO+H$^+$ requires 324.3266).

CH$_2$=CHCH$_2$NH derivative as illustrated in FIG. 4 prepared as described in the literature (Synth. Comm. 1996, 26, 2341–2348).

i-PrNMe derivative as illustrated in FIG. 4 Synthesized exactly as found in the general procedure for derivatives varying about carboxamide vida supra using i-Propyl-N-methyl-amine; all starting reagents were purchased from Aldrich, Acros, or Sigma.

Cyclopropylamine derivative as illustrated in FIG. 4 Synthesized exactly as found in the general procedure for derivatives varying about carboxamide vida supra using the cyclopropyl amine; all starting reagents were purchased from Aldrich, Acros, or Sigma.

Ph(CH$_2$)$_3$NH derivative as illustrated in FIG. 4 Synthesized exactly as found in the general procedure for derivatives varying about carboxamide vida supra using the commercially available Ph(CH$_2$)$_3$NH amine; all starting reagents were purchased from Aldrich, Acros, or Sigma.

BuNH derivative as illustrated in FIG. 4 Synthesized exactly as found in the general procedure for derivatives varying about carboxamide vida supra; all starting reagents were purchased from Aldrich, Acros, or Sigma: white solid: mp 30–31° C.; $^1$H NMR (CDCl$_3$, 400 MHz) δ 6.13 (br, 1H), 5.29–5.20 (m, 2H), 3.14 (q, 2H, J=5.9 Hz), 2.07 (t, 2H, J=7.6 Hz), 1.92–1.89 (m, 4H), 1.53 (p, 2H, J=6.8 Hz), 1.43–1.18 (m, 24H), 0.85–0.77 (m, 6H); $^{13}$C NMR (CDCl$_3$, 100 MHz) δ 173.1, 129.8, 129.5, 39.0, 36.6, 31.7, 31.6, 29.59, 29.55, 29.4, 29.2, 29.0, 27.03, 27.00, 25.7, 22.6, 19.9, 13.9, 13.5; IR (film) $υ_{max}$ 3301, 3084, 3001, 2954, 2918, 2849, 1639, 1559, 1466, 1231, 720 cm$^{-1}$; FABHRMS (NBA-NaI) m/z 338.3428 (C$_{22}$H$_{43}$NO+H$^+$ requires 338.3423).

Pyrrole derivative as illustrated in FIG. 4 Synthesized exactly as found in the general procedure for derivatives varying about carboxamide vida supra; all starting reagents were purchased from Aldrich, Acros, or Sigma: Pale yellow oil was purified by chromatography (33% EtOAc/hexanes) to afford desired product in quantitative yield. $^1$H NMR (CD$_3$OD, 400 MHz) δ 5.29–5.21 (m, 2H), 3.39 (t, 2H, J=6.7 Hz), 3.31 (t, 2H, J=6.9 Hz), 2.22 (t, 2H, J=7.6 Hz), 1.94 (m, 4H), 1.88 (p, 2H, J=6.7 Hz), 1.78 (p, 2H, J=6.9 Hz), 1.52 (p, 2H, J=7.2 Hz), 1.25–1.20 (m, 20H), 0.81 (t, 3H, J=6.8 Hz); $^{13}$C NMR (CD$_3$OD, 100 MHz) δ 173.9, 130.83, 130.79, 47.9, 46.8, 35.5, 33.1, 30.94, 30.90, 30.7, 30.54, 30.46, 30.3, 28.2, 27.0, 26.1, 25.4, 23.8, 14.7; IR (NaCl, film) $υ_{max}$ 2924, 2853, 1651, 1428, 1342, 1226, 1194, 723 cm$^{-1}$; HRFABMS m/z (M+Cs$^+$) 468.2225 (requires m/z 468.2242).

PhNH derivative as illustrated in FIG. 4 prepared as described in the literature (Synth. Comm. 1995, 25, 959–968).

NHOH derivative as illustrated in FIG. 4: prepared as previously described (JACS, 1996, 118, 5938–5945).

MeONMe derivative as illustrated in FIG. 4 Synthesized exactly as found in the general procedure for derivatives varying about carboxamide vida supra; all starting reagents were purchased from Aldrich, Acros, or Sigma:: Pale yellow oil was purified by chromatography (33% EtOAc/hexanes) to afford desired product in quantitative yield. $^1$H NMR (CD$_3$OD, 400 MHz) δ 5.34–5.26 (m, 2H), 3.66 (s, 3H), 3.12 (s, 3H), 2.39 (t, 3H, J=7.0 Hz), 1.99 (m, 4H), 1.56 (p, 2H, J=6.8 Hz), 1.30–1.26 (m, 20H), 0.86 (t, 3H, J=6.1 Hz); $^{13}$C NMR (CD$_3$OD, 100 MHz) δ 176.2, 130.9, 130.8, 61.8, 33.1, 32.7, 30.92, 30.88, 30.77, 30.54, 30.49, 30.45, 30.3, 28.2, 25.8, 23.8, 14.6; IR (NaCl, film) $υ_{max}$ 2923, 2853, 1673, 1463, 1413, 1383, 1177, 1116, 998, 722 cm$^{-1}$; HRFABMS m/z (M+H$^+$) 326.3072 (requires m/z 326.3059).

NH$_2$NH derivative as illustrated in FIG. 4: prepared as previously described (JACS, 1996, 118, 5938–5945).

MeO (methyl oleate) derivative as illustrated in FIG. 5 Synthesized exactly as found in the general procedure for derivatives varying about carboxamide vida supra; all starting reagents were purchased from Aldrich, Acros, or Sigma: The crude mixture was purified by chromatography (SiO$_2$, 5×15 cm, 1% EtOAc/hexanes) to afford quantitative yield of a clear oil. $^1$H NMR spectra agrees with spectra in Sadtler Handbook of NMR data. Additional data: $^{13}$C NMR (CD$_3$OD, 100 MHz) δ 176.0, 130.9, 130.8, 52.0, 34.8, 33.1, 30.9, 30.8, 30.6, 30.5, 30.4, 30.3, 30.20, 30.17, 28.14, 28.11, 26.1, 23.8, 14.5; IR (NaCl, film) υ$_{max}$ 2924, 2854, 1743, 1653, 1558, 1540, 1506, 1457, 1260, 1093, 1018, 801 cm$^{-1}$.

EtO (ethyl oleate) derivative as illustrated in FIG. 5 Synthesized exactly as found in the general procedure for derivatives varying about carboxamide vida supra; all starting reagents were purchased from Aldrich, Acros, or Sigma: clear oil. $^1$H NMR spectra agrees with spectra in Sadtler Handbook of NMR data. Additional data: $^{13}$C NMR (CD$_3$OD, 100 MHz) δ 173.8, 129.9, 129,7, 60.1, 34.3, 31.9, 29.7, 29.6, 29.5, 29.3, 29.12, 29.08, 29.05, 27.2, 27.1, 24.9, 22.6, 14.2, 14.1; IR (NaCl, film) υ$_{max}$ 2925, 2854, 1739, 1465, 1373, 1244, 1180, 1036, 723 cm$^{-1}$.

Me$_2$CHCH$_2$O derivative as illustrated in FIG. 5 Synthesized exactly as found in the general procedure for derivatives varying about carboxamide vida supra; all starting reagents were purchased from Aldrich, Acros, or Sigma: pale yellow oil. $^1$H NMR (CDCl$_3$, 400 MHz) δ 5.35–5.27 (m, 2H), 3.82 (d, 2H, J=3.4 Hz), 2.27 (t, 2H, J=7.5 Hz), 1.98–1.95 (m, 4H), 1.89 (septet, 1H, J=6.7 Hz), 1.59 (quintet, 2H, J=6.9 Hz), 1.27–1.23 (m, 20H), 0.90 (d, 6H, J=3.4 Hz), 0.85 (t, 3H, J=6.6 Hz); $^{13}$C NMR (CDCl$_3$, 100 MHz) δ 173.97, 129.92, 129.72, 70.36, 34.36, 31.89, 29.75, 29.67, 29.51, 29.31 (2), 29.15, 29.13, 29.09, 27.70, 27.19, 27.14, 25.02, 22.67, 19.07 (2), 14.10; IR (NaCl, film) υ$_{max}$ 2925.2; 2853.9, 1739.7, 1466.2, 1378.6, 1172.6, 1012.6; FABMS m/z (M+H$^+$) 339.

H(oleyl aldehyde) as illustrated in FIG. 5: prepared as described in the literature (JOC 1978, 43,2480–2482).

CF$_3$ as illustrated in FIG. 5: prepared as previously described (JACS, 1996, 118, 5938–5945).

ClCH$_2$ as illustrated in FIG. 5: prepared as previously described (JACS, 1996, 118, 5938–5945).

N$_2$CH as illustrated in FIG. 5: prepared as previously described (JACS, 1996, 118, 5938–5945).

Oleyl alcohol as illustrated in FIG. 5: prepared as described in the literature (JOC 1978, 43,2480–2482).

Oleyl acetate: purchased from Sigma

Oleyl amine: purchased from Pfaltz and Bauer

Oleyl aldehyde dimethyl acetal as illustrated in FIG. 5: prepared as described in the literature (J Med Chem, 1989, 32, 1319–1322).

CoA-SCO derivative as illustrated in FIG. 5: purchased from Sigma

HOCH$_2$CH$_2$NH derivative as illustrated in FIG. 6: Prepared as previously described. (JACS, 1996, 118, 580–590).

(HOCH$_2$CH$_2$)$_2$NH derivative as illustrated in FIG. 6: Purchased from Pfaltz and Bauer.

HOCH$_2$CH$_2$CH$_2$NH derivative as illustrated in FIG. 6 Synthesized exactly as found in the general procedure for derivatives varying about carboxamide vida supra; all starting reagents were purchased from Aldrich, Acros, or Sigma: white solid: mp 55–56° C.; $^1$H NMR (CDCl$_3$, 400 MHz) δ 6.87 (t, 1H, J=5.8 Hz), 5.28–5.19 (m, 2H), 4.25 (br, 1H), 3.52 (s, 2H), 3.27 (q, 2H, J=6.2 Hz), 2.09 (t, 2H, J=7.6 Hz), 1.91–1.88 (m, 4H), 1.58 (p, 4H, J=6.0 Hz), 1.51 (p, 2H, J=7.1 Hz), 1.20–1.17 (m, 20H), 0.78 (t, 3H, J=6.8 Hz); $^{13}$C NMR (CDCl$_3$, 100 MHz) δ 174.6, 129.8, 129.4, 58.9, 36.4, 36.0, 31.9, 31.7, 29.5, 29.3, 29.1, 29.0, 27.00, 26.96, 25.7, 22.5, 13.9; IR (film) υ$_{max}$ 3290, 2917, 2848, 1634, 1550, 1462, 1412, 1216, 1052, 762 cm$^{-1}$; FABHRMS (NBA-NaI) m/z 340.3226 (C$_{21}$H$_{41}$NO$_2$+H$^+$ requires 340.3216).

HOCH$_2$CH(OAc)CH$_2$O derivative as illustrated in FIG. 6: Purchased from Sigma HOCH$_2$CH$_2$NH derivative as illustrated in FIG. 6: Purchased from Sigma (HOCH$_2$CH$_2$)$_2$NH derivative as illustrated in FIG. 6 Synthesized exactly as found in the general procedure for derivatives varying about carboxamide vida supra; all starting reagents were purchased from Aldrich, Acros, or Sigma: orange oil; $^1$H NMR (CDCl$_3$, 500 MHz) δ 7.68 (br, 1H), 7.50 (br, 1H), 5.38–5.29 (m, 8H), 3.78 (t, 2H, J=5.0 Hz), 3.73 (t, 2H, J=5.3 Hz), 3.50 (t, 2H, J=5.0 Hz), 3.45 (t, 2H, J=5.0 Hz), 2.81–2.77 (m, 6H), 2.36 (t, 2H, J=7.5 Hz), 2.09 (q, 2H, J=6.0 Hz), 2.02 (q, 2H, J=7.0 Hz), 1.67 (p, 2H, J=7.5 Hz), 1.34–1.22 (m, 6H), 0.85 (t, 3H, J=6.8 Hz); $^{13}$C NMR (CDCl$_3$, 125 MHz) δ 175.3, 130.5, 129.2, 128.7, 128.5, 128.1 (2), 127.8, 127.4, 61.3, 60.7, 52.2, 50.5, 32.8, 31.4, 29.3, 27.2, 26.6, 25.6 (3), 25.0, 22.5, 14.0; IR (film) υ$_{max}$ 3375, 3011, 2956, 2926, 2857, 1727, 1621, 1455, 1270, 1072 cm$^{-1}$; FABHRMS (NBA-CSI) m/z 524.2152 (C$_4$H$_{41}$NO$_3$+Cs$^+$ requires 524.2141).

OH derivative as illustrated in FIG. 7: Oleic glycine ethyl ester (OEt) (725.5 mg, 1.97 mmol, 1 equiv) was dissolved in 6 mL of THF/MeOH/H$_2$O (3:1:1). The solution was treated with LiOH.H$_2$O (236.6 mg, 5.63 mmol, 2.9 equiv) and stirred at 25° C. for 15 minutes. The solution was diluted with 1N HCl (30 mL) and extracted with EtOAc (3×30 mL). The organic layers were dried over Na$_2$SO$_4$, filtered, and concentrated in vacuo to afford (611.2 mg, 91%) of OH as a white solid. $^1$H NMR (CDCl$_3$, 400 MHz) δ 7.04 (br, 1H), 6.26 (t, 1H, J=4.8 Hz), 5.36–5.27 (m, 2H), 4.04 (d, 2H, J=5.2 Hz), 2.24 (t, 3H, J=7.7 Hz), 1.97 (m, 4H), 1.61 (p, 2H, J=7.2 Hz), 1.27–1.24 (m, 20H), 0.85 (t, 3H, J=6.8 Hz); $^{13}$C NMR (CDCl$_3$, 100 MHz) δ 174.6, 172.7, 130.0, 129.7, 41.5, 36.3, 31.9, 29.74, 29.68, 29.5, 29.3 (2), 29.19, 29.15, 29.1, 27.20, 27.15, 25.5, 22.7, 14.1; IR (NaCl, film) υ$_{max}$ 3429, 3304, 2918, 2849, 1699, 1645, 1552, 1469, 1410, 1239, 718, 677 cm$^{-1}$; HRFABMS m/z (M+H$^+$) 340.2861 (requires m/z 340.2852); mp 90–91° C.

NH$_2$ derivative as illustrated in FIG. 7 Oleic glycine (OH) (325.6 mg, 0.96 mmol, 1 equiv), dry CH$_2$Cl$_2$ (16 mL), and concentrated ammonium hydroxide (225 μL) were combined under a N$_2$ atmosphere and cooled to 0° C. EDCI (573.1 mg, 1.93 mmol, 1 equiv) and DMAP (24.4 mg, 0.20 mmol, 0.2 equiv) were added and the reaction was stirred at 25° C. for 2.5 h. The solvent was removed in vacuo and the crude product was purified by chromatography (SiO$_2$, 3×18 cm, 0–10% methanol/EtOAc, gradient elution) to afford 231.1 mg (71%) of NH$_2$ as a white solid. $^1$H NMR (CD$_3$OD, 400 MHz) δ 8.03 (br, 1H), 5.28–5.20 (m, 2H), 3.72 (d, 2H, J=1.4 Hz), 2.16 (t, 2H, J=7.6 Hz), 1.92 (m, 4H), 1.52 (p, 2H, J=7.2 Hz), 1.23–1.19 (m, 20H), 0.80 (t, 3H, J=6.9 Hz); $^{13}$C NMR (CDCl$_3$, 100 MHz) δ 173.8, 171.0, 130.0, 129.7, 42.8, 36.4, 31.9, 29.8, 29.7, 29.5, 29.3, 29.2, 29.1, 27.21, 27.16, 25.6, 22.7, 14.1; IR (NaCl, film) υ$_{max}$ 3385, 3307, 3195, 2918, 2849, 1661, 1643, 1549, 1468, 1415 cm$^{-1}$; HRFABMS m/z (M+H$^+$) 339.3020 (requires m/z 339.3012); mp 124–125° C.

OEt derivative as illustrated in FIG. 7: Oleic acid (100 μL, 0.32 mmol, 1 equiv), glycine ethyl ester hydrochloride (45.9 mg, 0.33 mmol, 1 equiv), dry triethylamine (66 μL, 47 mmol, 1.5 equiv) and dry methylene chloride (5 mL) were combined under a N$_2$ atmosphere and cooled to 0° C. EDCI (107.0 mg, 0.36 mmol, 1.1 equiv) and DMAP (8.1 mg, 0.07 mmol, 0.2 equiv) were added and the reaction was allowed to stir at 25° C. for 4 h. The solvent was removed in vacuo and the crude product was chromatographed ($SiO_2$, 2×15 cm, 20%–33% EtOAc/hexanes, gradient elution) to afford OEt as a white solid (109.5 mg, 94%). $^1$H NMR ($CDCl_3$, 400 MHz) δ 5.95 (br, 1H), 5.36–5.27 (m, 2H), 4.19 (quartet, 2H, J=7.1 Hz), 4.00 (d, 2H, J=5.1 Hz), 2.21 (t, 2H, J=7.6 Hz), 1.99 (m, 4H), 1.62 (p, 2H, J=7.2 Hz), 1.28–1.24 (m, 23H), 0.85 (t, 3H, J=6.8 Hz); $^{13}$C NMR ($CDCl_3$, 100 MHz) δ 173.2, 170.1, 130.0, 129.7, 61.5, 41.3, 36.4, 31.9, 29.73, 29.67, 29.5, 29.3, 29.2, 29.1, 27.2, 27.1, 25.5, 22.7, 14.1; IR (NaCl, film) $\upsilon_{max}$ 3311, 2918, 2849, 1739, 1647, 1552, 1465, 1413, 1375, 1213, 1032, 700 cm$^{-1}$; HRFABMS m/z (M+H$^+$) 368.3175 (requires m/z 368.3165); mp 32–33° C.

OH/$R_1$=Me derivative as illustrated in FIG. 7: purchased from Sigma.

OEt/$R_1$=Me derivative as illustrated in FIG. 7: (both isomers): To a solution of oleoyl sarcosine (OH) (200.7 mg, 0.57 mmol, 1 eq) in anhydrous THF (6 mL) was added DCC (158.9 mg, 0.77 mmol, 1.4 eq) and absolute EtOH (50 µL, 0.85 mmol, 1.5 eq). The reaction mixture was stirred at 25° C. for 22 h. The white precipitate was filtered off and water (30 mL) was added to the eluent. The aqueous layer was extracted with EtOAc (3×30 mL). The organic layers were dried ($Na_2SO_4$), filtered, and concentrated in vacuo. The crude product was chromatographed ($SiO_2$, 3×15 cm, 10–50% EtOAc/hexanes, gradient elution) to afford clear oil OEt (150.8 mg, 70%) as a mixture of isomers; $^1$H NMR ($CDCl_3$, 400 MHz) δ 5.30–5.27 (m, 2H), 4.19–4.09 (m, 2H), 4.05+3.97 (s, 2H), 3.01+2.91 (s, 3H), [2.31 (t, J=7.5 Hz)+ 2.16 (t, J=7.4 Hz)] [2H], 1.96–1.94 (m, 2H), 1.59 (p, 2H, J=6.6 Hz), 1.26–1.20 (m, 23H), 0.82 (t, 3H, J=6.0 Hz); $^{13}$C NMR ($CDCl_3$, 100 MHz) major isomer (minor isomer) δ 173.7 (173.3), 169.3 (169.0), 129.8, 129.7, (127.9, 127.8), (61.4), 60.9, (51.6), 49.3, 36.4, (34.7), 33.0, (32.8, 32.5), 31.8, (31.4), 29.64, 29.60, 29.4, 29.23, 29.19, 29.0, 27.1, (24.9), 24.8, 22.6, 14.03, 13.99; IR (film) $\upsilon_{max}$ 2924, 2853, 1750, 1655, 1465, 1400, 1373, 1197, 1113, 1035 cm$^{-1}$; FABHRMS (NBA-NaI) m/z 404.3128 ($C_{23}H_{43}O_3N+Na^+$ requires 404.3141).

$CH_2OCH_3$ derivative as illustrated in FIG. 8. A solution of 18-TBDPS-acid (prepared as described in JACS, 1996, 118, 580–590)(390.1 mg, 0.58 mmol, 1 eq) in THF (2 mL) under N$_2$ at 25° C. was treated with TBAF (1M in THF, 1.2 mL, 1.2 mmol, 2 eq) for 2 h. Water (30 mL) was added and the aqueous layer was extracted with EtOAc (3×30 mL). The organic layers were dried ($Na_2SO_4$), filtered, and concentrated in vacuo. The crude product was chromatographed ($SiO_2$, 2×8 cm, 20–100% EtOAc/hexanes, gradient elution) to afford 18-OH-acid (149.1 mg, 86%) as a white solid: 25° C.; $^1$H NMR ($CDCl_3$, 400 MHz) δ 6.47 (br, 1H), 5.35–5.26 (m, 2H), 3.60 (t, 2H, J=6.7 Hz), 2.29 (t, 2H, J=7.5 Hz), 1.98–1.95 (m, 4H), 1.60–1.49 (m, 4H), 1.27 (s, 18H); $^{13}$C NMR ($CDCl_3$, 100 MHz) δ 179.2, 129.9, 129.8, 62.8, 34.1, 32.5, 29.7, 29.6, 29.4, 29.3, 29.2, 29.1, 29.0 (2), 27.11, 27.07, 25.7, 24.7; IR (film) $\upsilon_{max}$ 3355, 2926, 2853, 1710, 1462, 1409, 1246, 1054, 722 cm$^{-1}$; FABHRMS (NBA-NaI) m/z 321.2415 ($C_{18}H_{34}O_3+Na^+$ requires 321.2406).

A solution of 18-OH-acid (67.7 mg, 0.23 mmol, 1 eq) in anhydrous THF (2.2 mL) under N$_2$ at 0° C. was treated with NaH (60%, 28.1 mg, 0.70 mmol, 3 eq) for 15 min. MeI (72 µL, 1.16 mmol, 5 eq) was added and the reaction was warmed to 25° C. and allowed to stir for 5 h. A second portion of MeI (140 µL, 2.25 mmol, 10 eq) was added and the reaction was stirred for an additional 14 h. Water (30 mL) was added and the aqueous layer was extracted with EtOAc (3×30 mL). The organic layers were dried ($Na_2SO_4$), filtered, and concentrated in vacuo. The crude product was chromatographed ($SiO_2$, 2×8 cm, 20–100% EtOAc/hexanes, gradient elution) to afford 18-methoxy-acid (41.0 mg, 58%) as a clear oil; $^1$H NMR ($CDCl_3$, 400 MHz) δ 5.35–5.27 (m, 2H), 3.35 (t, 2H, J=6.7 Hz), 3.31 (s, 3H), 2.31 (t, 2H, J=7.5 Hz), 1.99–1.96 (m, 4H), 1.64–1.50 (m, 4H), 1.28–1.27 (m, 18H); $^{13}$C NMR ($CDCl_3$, 100 MHz) δ 179.7, 129.9, 129.7, 73.0, 58.4, 34.0, 29.7, 29.6, 29.5, 29.4, 29.2, 29.1, 29.0, 27.2, 27.1, 26.1, 24.7; IR (film) $\upsilon_{max}$ 2926, 2854, 1710, 1458, 1119 cm$^{-1}$; FABHRMS (NBA-NaI) m/z 335.2568 ($C_{19}H_{36}O_3+Na^+$ requires 335.2562).

A solution of 18-methoxy-acid (37.7 mg, 0.12 mmol, 1 eq) in anhydrous $CH_2Cl_2$ (0.6 mL) under N$_2$ at 0° C. was treated with oxalyl chloride (2M in $CH_2Cl_2$, 0.18 mL, 0.36 mmol, 3 eq). The reaction mixture was warmed to 25° C. and stirred for 3 h before the solvent was removed in vacuo. The residue was cooled to 0° C. and treated with excess concentrated $NH_4OH$ (1 mL). Water (30 mL) was added and the aqueous layer was extracted with EtOAc (3×30 mL). The organic layers were dried ($Na_2SO_4$), filtered, and concentrated in vacuo. The crude product was chromatographed ($SiO_2$, 2×5 cm, 50–100% EtOAc/hexanes, gradient elution) to afford $CH_2OCH_3$ (34.6 mg, 92%) as a white solid: mp 59–60° C.; $^1$H NMR ($CDCl_3$, 400 MHz) δ 5.71 (br, 1H), 5.52 (br, 1H), 5.35–5.27 (m, 2H), 3.33 (t, 2H, J=6.7 Hz), 3.29 (s, 3H), 2.18 (t, 2H, J=7.6 Hz), 1.98–1.96 (m, 4H), 1.61–1.49 (m, 4H), 1.27–1.26 (m, 18H); $^{13}$C NMR ($CDCl_3$, 100 MHz) δ 175.8, 129.9, 129.8, 72.9, 58.5, 35.9, 29.7, 29.64, 29.60, 29.4, 29.20, 29.18, 29.07, 27.14, 27.12, 26.1, 25.5; IR (film) $\upsilon_{max}$ 3356, 3191, 2922, 2851, 2358, 1660, 1633, 1469, 1410, 1120 cm$^{-1}$; FABHRMS (NBA-NaI) m/z 334.2730 ($C_{19}H_{37}O_2N+Na^+$ requires 334.2722).

$CH_2OH$ derivative as illustrated in FIG. 8 is commercially available from Aldrich.

$CONH_2$ derivative as illustrated in FIG. 8 and scheme shown in FIG. 19 (left side): A solution of $CO_2H$ (73.8 mg, 0.24 mmol, 1 eq) in anhydrous $CH_2Cl_2$ (1.2 mL) under N$_2$ at 0° C. was treated with oxalyl chloride (2M in $CH_2Cl_2$, 0.36 mL, 0.72 mmol, 3 eq). The reaction mixture was warmed to 25° C. and stirred for 3 h in the dark before the solvent was removed in vacuo. The residue was cooled to 0° C. and treated with excess concentrated $NH_4OH$ (3 mL). Water (30 mL) was added and the aqueous layer was extracted with EtOAc (3×30 mL) and $CHCl_3$(3×30 mL). The organic layers were dried ($Na_2SO_4$), filtered, and concentrated in vacuo. The crude product was chromatographed ($SiO_2$, 2×15 cm, 0–10% MeOH/EtOAc, gradient elution) to afford $CONH_2$ (27.8 mg, 38%) as a white solid: mp 128–129° C.; $^1$H NMR ($CDCl_3$, 400 MHz) δ 5.47 (br, 4H), 5.35–5.28 (m, 2H), 2.20 (t, 4H, J=7.6 Hz), 1.98 (q, 4H, J=5.6 Hz), 1.61 (p, 4H, J=7.3 Hz), 1.29 (s, 12H); $^{13}$C NMR ($CDCl_3$, 100 MHz) δ 175.6 (2), 129.9 (2), 35.9 (2), 29.6 (2), 29.2 (4), 29.0 (2), 27.1 (2), 25.5 (2); IR (film) $\upsilon_{max}$ 3385, 3186, 2921, 2848, 1647, 1419 cm$^{-1}$; FABHRMS (NBA-NaI) m/z 311.2691 ($C_{18}H_{34}N_2O_2+H^+$ requires 311.2699).

$CO_2H$ derivative as illustrated in FIG. 8: A solution of 18-hydroxy-amide (prepared as described in JACS, 1996, 118, 580–590)(101.2 mg, 0.34 mmol, 1 eq) in anhydrous DMF (3.4 mL) under N$_2$ was treated with PDC (644.0 mg, 1.71 mmol, 5 eq) at 25° C. for 5 h. Water (30 mL) was added and the mixture was extracted with EtOAc (3×30 mL). The organic layers were dried ($Na_2SO_4$), filtered, and concentrated in vacuo. The crude product was chromatographed ($SiO_2$, 2.5×15 cm, 5–10% EtOAc/hexanes, gradient elution) to afford $CO_2H$ (85.0 mg, 80%) as a white solid: mp 74–76° C.; $^1$H NMR ($CDCl_3$, 400 MHz) δ 6.71 (br, 1H), 5.74 (br, 1H), 5.34–5.27 (m, 2H), 2.29 (t, 2H, J=7.5 Hz), 2.19 (t, 2H, J=7.6 Hz), 1.97 (m, 4H), 1.59 (m, 4H), 1.27 (s, 16H); $^{13}$C NMR (CDCl$_3$, 100 MHz) δ 178.6, 177.5, 129.9, 129.8, 35.9, 34.2, 29.6, 29.5, 29.2, 29.10, 29.08, 29.02 (2), 28.9, 27.1, 27.0, 25.5, 24.8; IR (film) υ$_{max}$ 3389, 3191, 3008, 2917, 2848, 1704, 1645, 1466, 1417 cm$^{-1}$; FABHRMS (NBA-CsI) m/z 444.1524 (C$_{18}$H$_{33}$NO$_3$+Cs$^+$ requires 444.1515)

Compound 2: (9-octadecynamide) derivative as illustrated in FIG. 9 Synthesized exactly as found in the general procedure prepared in a manner analogous to 6 (infra); all starting reagents were purchased from Aldrich, Acros, or Sigma: mp 91–92° C.; $^1$H NMR (CDCl$_3$, 400 MHz) δ 6.14 (br, 1H), 5.62 (br, 1H), 2.15 (t, 2H, J=7.6 Hz), 2.07 (t, 4H, J=7.0 Hz), 1.57 (p, 2H, J=7.1 Hz), 1.41 (p, 4H, J=7.4 Hz), 1.35–1.21 (m, 16H), 0.82 (t, 3H, J=6.9 Hz); $^{13}$C NMR (CDCl$_3$, 100 MHz) δ 176.0, 80.2, 80.0, 35.9, 31.8, 29.1, 29.04 (3), 28.98, 28.8 (2), 28.6, 25.4, 22.6, 18.7, 18.6, 14.0; IR (film) υ$_{max}$ 3409, 2928, 2850, 1647, 1471, 1419, 712 cm$^{-1}$; FABHRMS (NBA-CsI) m/z 412.1636 (C$_{18}$H$_{33}$NO+Cs$^+$ requires 412.1616).

3 derivative as illustrated in FIG. 9: Prepared as previously described. (JACS, 1996, 118, 580–590).

4 derivative as illustrated in FIG. 9: Prepared as described in the literature (JACS, 1959, 81, 4256).

5 derivative as illustrated in FIG. 9 Synthesized exactly as found in the general procedure prepared in a manner analogous to 6; all starting reagents were purchased from Aldrich, Acros, or Sigma: mp 47–48° C.; $^1$H NMR (CDCl$_3$, 400 MHz) δ 7.13–7.07 (m, 4H), 5.53 (br, 1H), 5.41 (br, 1H), 2.57 (td, 4H, J=7.9, 1.5 Hz), 2.20 (t, 2H, J=7.6 Hz), 1.62 (p, 2H, J=7.1 Hz), 1.55 (p, 4H, J=7.8 Hz), 1.34–1.26 (m, 16H), 0.86 (t, 3H, J=6.8 Hz); $^{13}$C NMR (CDCl$_3$, 100 MHz) δ 175.6, 140.5, 140.4, 129.1, 129.0, 125.70, 125.66, 35.9, 32.7, 32.6, 31.9, 31.3, 31.2, 29.8, 29.6, 29.5, 29.3 (2), 29.2, 25.5, 22.7, 14.1; IR (film) υ$_{max}$ 3392, 3194, 2924, 2853, 1647, 1464, 1415, 746 cm$^{-1}$; FABHRMS (NBA-NaI) m/z 354.2776 (C$_{22}$H$_{37}$NO requires 354.2773).

6 derivative as illustrated in FIG. 9: A solution of 1-bromopentane (1.0 mL, 8.1 mmol, 1 eq) and Ph$_3$P (2.32 g, 8.8 mmol, 1.1 eq) in anhydrous CH$_3$CN (6 mL) under N$_2$ was refluxed for 20 h. The reaction mixture was concentrated in vacuo and the crude product was chromatographed (SiO$_2$, 3×20 cm, 10% EtOAc/hexanes-50% iPrOH/EtOAc, gradient elution) to afford phosphonium salt (3.27 g, 98%) as a white foam; $^1$H NMR (CDCl$_3$, 400 MHz) δ 7.84–7.73 (m, 9H), 7.69–7.65 (m, 6H), 3.78–3.71 (m, 2H), 1.58–1.57 (m, 4H), 1.25 (s, 2H, J=7.2 Hz), 0.78 (t, 3H, J=7.3 Hz); $^{13}$C NMR (CDCl$_3$, 100 MHz) δ 134.9 (3, d, J=2 Hz), 133.6 (6, d, J=10 Hz), 130.4 (6, d, J=12 Hz), 118.3 (3, d, J=86 Hz), 32.3 (d, J=15 Hz), 22.9, 22.3, 22.2 (d, J=3 Hz), 13.6; IR (film) υ$_{max}$ 3405, 2921, 2864, 1438, 1112, 996, 749, 723, 690 cm$^{-1}$; ESI (M-Br$^+$) 333.

A solution of phosphonium salt (3.2 g, 7.74 mmol, 1.1 eq) in anhydrous THF (60 mL) under N$_2$ at −78° C. was treated with n-BuLi (2.0M, 7.0 mL, 14.0 mmol, 2.0 eq). The reaction mixture was warmed to 25° C. and allowed to stir for 10 min. The reaction was recooled to −78° C. and treated with a solution of 2-cyanobenzaldehyde (0.9119 g, 6.95 mmol, 1 eq) in anhydrous THF (15 mL). The reaction mixture was then warmed to 25° C. and stirred for 1 h before an aqueous solution of saturated NH$_4$Cl (100 mL) was added. The aqueous layer was extracted with EtOAc (3×100 mL) and the organic layers were dried (Na$_2$SO$_4$), filtered, and concentrated in vacuo. The crude product was chromatographed (SiO$_2$, 6×20 cm, 0–5% EtOAc/hexanes, gradient elution) to afford CN-alkene (0.9796 g, 76%) as a clear oil (mixture of E/Z isomers); $^1$H NMR (CDCl$_3$, 400 MHz) δ 7.64–7.22 (m, 4H), [6.72 (d, J=15.7 Hz)+6.59 (d, J=11.6 Hz)][1H], [6.41 (dt, J=15.7, 7.0 Hz)+5.90 (dt, J=11.6, 7.5 Hz)][1H], [2.27 (qd, J=7.6, 1.4 Hz)+2.21 (qd, J=7.3, 1.7 Hz)][2H], 1.50–1.20 (m, 4H), [0.91 (t, J=7.2 Hz)+0.84 (t, J=7.2 Hz)][3H]; $^{13}$C NMR (CDCl$_3$, 100 MHz) δ 141.3, 141.2, 137.4, 136.8, 132.8, 132.7, 132.6, 132.2, 129.4, 126.8, 125.8, 125.3, 125.0, 118.1, 118.0, 112.2, 110.4, 32.8, 31.6, 31.1, 28.4, 22.2, 13.9, 13.8; IR (film) υ$_{max}$ 2957, 2928, 2858, 2224, 1647, 1596, 1478, 1466, 1448, 966, 759 cm$^{-1}$; FABHRMS (NBA-NaI) m/z 186.1285 (C$_{13}$H$_{15}$N+H$^+$ requires 186.1283).

A solution of CN-alkene (0.9394 g, 5.1 mmol, 1 eq) in anhydrous toluene (10 mL) under N$_2$ at 0° C. was treated with DIBAL (1M, 5.6 mL, 5.6 mmol, 1.1 eq). The reaction mixture was stirred for 5 min before an aqueous saturated solution of NH$_4$Cl (60 mL) was added. The mixture was stirred at 25° C. for 15 min before the aqueous layer was extracted with EtOAc (3×60 mL). The organic layers were dried (Na$_2$SO$_4$), filtered, and concentrated in vacuo. The crude product was chromatographed (SiO$_2$, 4×20 cm, 0–4% EtOAc/hexanes, gradient elution) to afford CHO-alkene (0.86 g, 91%) as a clear oil (mixture of E/Z isomers); $^1$H NMR (CDCl$_3$, 400 MHz) δ [10.26+10.22][s, 1H], [7.87 (dd, J=7.8, 1.4 Hz)+7.77 (dt, J=7.6, 0.9 Hz)][1H], 7.54–7.23 (m, 3H), [7.15 (dt, J=15.6, 1.5 Hz)+6.77 (d, J=11.5 Hz)][1H], [6.13 (dt, J=15.6, 6.9 Hz)+5.90 (dt, J=11.5, 7.5 Hz)][1H], [2.26 (qd, J=7.5, 1.5 Hz)+2.03 (qd, J=7.3, 1.6 Hz)][2H], 1.50–1.18 (m, 4H), [0.91 (t, J=7.3 Hz)+0.79 (t, J=7.3 Hz)][3H]; $^{13}$C NMR (CDCl$_3$, 100 MHz) δ 192.4, 141.0, 137.5, 136.2, 133.6, 133.5, 132.5, 130.5, 130.4, 128.4, 127.4, 127.1, 126.9, 125.6, 125.1, 33.0, 31.4, 31.2, 28.1, 22.21, 22.16, 13.9, 13.8; IR (film) υ$_{max}$ 2957, 2928, 2871, 1695, 1597, 1566, 1480, 1466, 1451, 1389, 1289, 1196, 968, 762 cm$^{-1}$; FABHRMS (NBA-NaI) m/z 189.1280 (C$_{13}$H$_{16}$O+H$^+$ requires 189.1279).

A solution of 5-bromo-pentanol (0.9889 g, 5.9 mmol, 1 eq) in anhydrous CH$_2$Cl$_2$ (20 mL) under N$_2$ at 25° C. was treated with anhydrous Et$_3$N (1.0 mL, 7.2 mmol, 1.2 eq), TBDPSCl (1.7 mL, 6.5 mmol, 1.1 eq) and DMAP (0.23 g, 1.9 mmol, 0.3 eq). The reaction mixture was stirred for 2 h before an aqueous solution of saturated NH$_4$Cl (100 mL) was added. The aqueous layer was extracted with EtOAc (3×100 mL) and the organic layers were dried (Na$_2$SO$_4$), filtered, and concentrated in vacuo. The crude product was chromatographed (SiO$_2$, 5×20 cm, 0–20% EtOAc/hexanes, gradient elution) to afford TBDPSOH (2.35 g, 98%) as a clear oil; $^1$H NMR (CDCl$_3$, 400 MHz) δ 7.66–7.60 (m, 4H), 7.44–7.33 (m, 6H), 3.64 (t, 2H, J=6.1 Hz), 3.37 (t, 2H, J=6.9 Hz), 1.82 (p, 2H, J=7.3 Hz), 1.59–1.45 (m, 4H), 1.03 (s, 9H); $^{13}$C NMR (CDCl$_3$, 100 MHz) δ 135.6, 129.6, 127.6, 127.5, 63.5, 33.9, 32.5, 31.6, 26.8, 24.5, 19.2; IR (film) υ$_{max}$ 3069, 2930, 2856, 2359, 1470, 1427, 1389, 1106, 822, 738, 700 cm$^{-1}$; FABHRMS (NBA-CsI) m/z 537.0235 (C$_{21}$H$_{29}$OSiBr+Cs$^+$ requires 537.0225).

A solution of TBDPSOH(2.35 g, 5.8 mmol, 1 eq) and Ph$_3$P (1.67 g, 6.4 mmol, 1.1 eq) in anhydrous CH$_3$CN (6 mL) under N$_2$ was refluxed for 22 h. The reaction mixture was concentrated in vacuo and the crude product was chromatographed (SiO$_2$, 5×20 cm, 20% EtOAc/hexanes-50% iPrOH/EtOAc, gradient elution) to afford TBDPSphosphonium salt (2.82 g, 73%) as a white foam; $^1$H NMR (CDCl$_3$, 400 MHz) δ 7.84–7.72 (m, 9H), 7.67–7.62 (m, 6H), 7.58–7.55 (m, 4H), 7.38–7.29 (m, 6H), 3.84 (m, 2H), 3.57 (t, 2H, J=6.3 Hz), 1.75–1.51 (m, 6H), 0.95 (s, 9H); $^{13}$C NMR (CDCl$_3$, 100 MHz) δ 135.4 (4), 134.9 (3, d, J=3 Hz), 133.8 (2), 133.7 (6, d, J=10 Hz), 130.4 (6, d, J=13 Hz), 129.5 (2), 127.6 (4), 118.3 (3, d, J=85 Hz), 63.4, 31.9, 15 26.8 (3), 25.3, 23.0, 22.4 (d, J=3 Hz), 19.1; IR (film) υ$_{max}$ 3394, 2928, 2856, 2359, 1438, 1111, 996, 743, 703, 689 cm$^{-1}$; ESI (M-Br$^+$) 587.

A solution of TBDPSphosphonium salt (2.5783 g, 3.9 mmol, 1.1 eq) in anhydrous THF (25 mL) under N$_2$ at −78°

C. was treated with n-BuLi (2.0M, 3.5 mL, 7.0 mmol, 2 eq). The reaction mixture was warmed to 25° C. and allowed to stir for 10 min. The reaction was recooled to −78° C. and treated with a solution of CHO-alkene (0.66 g, 3.5 mmol, 1 eq) in anhydrous THF (10 mL). The reaction mixture was then warmed to 25° C. and stirred for 1 h before an aqueous solution of saturated NH$_4$Cl (60 mL) was added. The aqueous layer was extracted with EtOAc (3×60 mL) and the organic layers were dried (Na$_2$SO$_4$), filtered, and concentrated in vacuo. The crude product was chromatographed (SiO$_2$, 3×20 cm, 0–20% EtOAc/hexanes, gradient elution) to afford alkene-alkene (0.57 g, 33%) as a clear oil (mixture of E/Z isomers); $^1$H NMR (CDCl$_3$, 400 MHz) δ 7.67–7.57 (m, 4H), 7.45–7.33 (m, 7H), 7.24–7.09 (m, 3H), 6.63–6.35 (m, 2H), 6.14–5.61 (m, 2H), 3.70–3.58 (m, 2H), 2.21–2.06 (m, 4H), 1.64–1.23 (m, 8H), 1.04–1.01 (m, 9H), 0.94–0.80 (m, 3H); $^{13}$C NMR (CDCl$_3$, 100 MHz) δ 136.6, 136.5, 135.5, 134.1, 133.2, 133.0, 132.8, 129.5, 129.1, 129.0, 128.0, 127.8, 127.6, 126.8, 126.2, 125.3, 63.7, 33.0, 32.2, 32.1, 32.0, 28.19, 28.15, 26.8, 26.0, 25.9, 25.7, 22.3, 19.2, 13.9; IR (film) υ$_{max}$ 2929, 2857, 1473, 1428, 1111, 823, 740, 701 cm$^{-1}$; FABHRMS (NBA-CsI) m/z 629.2226 (C$_{34}$H$_{44}$OSi+Cs$^+$ requires 629.2216).

Alkene-alkene (0.4311 g, 0.87 mmol, 1 eq) was combined with 10% Pd/C (0.33 g) under Ar. Absolute EtOH (8 mL) was added and the atmosphere was purged to H$_2$. The reaction was stirred at 25° C. for 24 h. The crude product was filtered through Celite to afford alkane (347.3 mg, 80%) as a clear oil; $^1$H NMR (CDCl$_3$, 400 MHz) δ 7.84–7.78 (m, 4H), 7.56–7.44 (m, 6H), 7.27–7.21 (m, 4H), 3.80 (t, 2H, J=6.5 Hz), 2.73 (td, 4H, J=7.9, 2.4 Hz), 1.70 (m, 6H), 1.58–1.42 (m, 10H), 1.19 (s, 9H), 1.02 (t, 3H, J=7.0 Hz); $^{13}$C NMR (CDCl$_3$, 100 MHz) δ 140.5, 140.4, 135.6, 134.1, 129.5, 129.1, 127.6, 125.7, 63.9, 32.7, 32.6, 32.5, 31.7, 31.3, 29.50, 29.46, 26.9, 25.7, 22.6, 19.2, 14.1; IR (film) υ$_{max}$ 3070, 2928, 2856, 1956, 1888, 1823, 1589, 1471, 1427, 1389, 1361, 1188, 1111, 1007, 939, 910, 823, 740, 701, 614 cm$^{-1}$; FABHRMS (NBA-CsI) m/z 633.2525 (C$_{34}$H$_{48}$OSi+Cs$^+$ requires 633.2529).

A solution of alkane (325.7 mg, 0.65 mmol, 1 eq) in anhydrous THF (6 mL) under N$_2$ was treated with TBAF (1M in THF, 1.3 mL, 1.3 mmol, 2 eq) and stirred at 25° C. for 1.5 h. Water (30 mL) was added and the aqueous layer was extracted with EtOAc (3×30 mL). The organic layers were dried (Na$_2$SO$_4$), filtered, and concentrated in vacuo. The crude product was chromatographed (SiO$_2$, 2.5×15 cm, 10–33% EtOAc/hexanes, gradient elution) to afford alcohol (142.7 mg, 84%) as a clear oil; $^1$H NMR (CDCl$_3$, 400 MHz) δ 7.18–7.11 (m, 4H), 3.64 (t, 2H, J=6.6 Hz), 2.66–2.61 (m, 4H), 1.64–1.57 (m, 6H), 1.45–1.32 (m, 10H), 0.94 (t, 3H, J=6.9 Hz); $^{13}$C NMR (CDCl$_3$, 100 MHz) δ 140.4, 140.2, 129.02, 128.98, 125.7, 125.6, 62.7, 32.6 (2), 32.5, 31.7, 31.22, 31.20, 29.5, 29.4, 25.6, 22.6, 14.0; IR (film) υ$_{max}$ 3340, 2928, 2856, 1489, 1463, 1055, 750 cm$^{-1}$; FABHRMS (NBA-NaI) m/z 262.2308 (C$_{18}$H$_{30}$O+$^+$ requires 262.2297).

A solution of alcohol (128.9 mg, 0.49 mmol, 1 eq) in anhydrous DMF (1 mL) under N$_2$ was treated with PDC (0.91 g, 2.4 mmol, 5 eq) at 25° C. for 8 h. Water (30 mL) was added and the aqueous layer was extracted with EtOAc (3×30 mL). The organic layers were dried (Na$_2$SO$_4$), filtered, and concentrated in vacuo. The crude product was chromatographed (SiO$_2$, 2.5×15 cm, 20–50% EtOAc/hexanes, gradient elution) to afford acid (88.1 mg, 65%) as a clear oil; $^1$H NMR (CDCl$_3$, 400 MHz) δ 7.16–7.10 (m, 4H), 2.61 (q, 4H, J=7.2 Hz), 2.37 (t, 2H, J=7.5 Hz), 1.70 (p, 2H, J=77 Hz), 1.59 (septet, 4H, J=7.7 Hz), 1.48–1.30 (m, 8H), 0.90 (t, 3H, J=7.0 Hz); $^{13}$C NMR (CDCl$_3$, 100 MHz) δ 180.3, 140.5, 140.0, 129.1, 129.0, 125.8, 125.7, 34.0, 32.7, 32.4, 31.7, 31.3, 30.9, 29.4, 29.1, 24.6, 22.6, 14.0; IR (film) υ$_{max}$ 2928, 2858, 2359, 1709, 1489, 1462, 1412, 1287, 1242, 941, 751 cm$^{-1}$; FABHRMS (NBA-NaI) m/z 299.1976 (C$_{18}$H$_{28}$O$_2$+Na$^+$ requires 299.1987).

A solution of acid (62.3 mg, 0.23 mmol, 1 eq) in anhydrous CH$_2$Cl$_2$ (1.2 mL) under N$_2$ at 0° C. was treated with oxalyl chloride (2M in CH$_2$Cl$_2$, 0.34 mL, 0.68 mmol, 3 eq). The reaction mixture was warmed to 25° C. and stirred for 3 h before the solvent was removed in vacuo. The residue was cooled to 0° C. and treated with excess concentrated NH$_4$OH (5 mL). Water (30 mL) was added and the aqueous layer was extracted with EtOAc (3×30 mL). The organic layers were dried (Na$_2$SO$_4$), filtered, and concentrated in vacuo. The crude product was chromatographed (SiO$_2$, 2.5×15 cm, 33–66% EtOAc/hexanes, gradient elution) to afford 6 (36.9 mg, 59%) 25 as a white solid; mp 58–59° C.; $^1$H NMR (CDCl$_3$, 400 MHz) δ 7.14–7.08 (m, 4H), 5.91 (br, 1H), 5.49 (br, 1H), 2.58 (q, 4H, J=6.4 Hz), 2.20 (t, 2H, J=7.6 Hz), 1.66 (hextet, 2H, J=7.7 Hz), 1.55 (hex, 4H, J=8.4 Hz), 1.45–1.28 (m, 8H), 0.88 (t, 3H, J=6.8 Hz); $^{13}$C NMR (CDCl$_3$, 100 MHz) δ 175.7, 30 140.5, 140.0, 129.1, 129.0, 125.8, 125.7, 35.8, 32.6, 32.4, 31.7, 31.2, 30.9, 29.4, 29.2, 25.4, 22.6, 14.1; IR (film) υ$_{max}$ 3366, 3195, 2925, 2855, 1664, 1629, 1491, 1465, 1412, 750 cm$^{-1}$; FABHRMS (NBA-NaI) m/z 276.2329 (C$_{18}$H$_{29}$ON+H$^+$ requires 276.2327).

7 derivative as illustrated in FIG. 9 Synthesized exactly as found in the general procedure prepared in a manner analogous to 6; all starting reagents were purchased from Aldrich, Acros, or Sigma: white solid; mp 95–96° C.; $^1$H NMR (CDCl$_3$, 400 MHz) δ 7.06 (s, 4H), 5.58 (br, 1H), 5.40 (br, 1H), 2.54 (t, 4H, J=7.8 Hz), 2.18 (t, 2H, J=7.6 Hz), 1.57 (m, 6H), 1.35–1.25 (m, 12H), 0.86 (t, 3H, J=6.9 Hz); $^{13}$C NMR (CDCl$_3$, 100 MHz) δ 175.6, 140.2, 139.7, 128.22 (2), 128.19 (2), 35.9, 35.5, 35.4, 31.8, 31.6, 31.3, 29.3, 29.2, 29.0, 28.9, 25.4, 22.7, 14.1; IR (film) υ$_{max}$ 3388, 3187, 2923, 2851, 1645, 1514, 1463, 1416, 1121, 810 cm$^{-1}$; FABHRMS (NBA-NaI) m/z 304.2651 (C$_{20}$H$_{33}$ON+H$^+$ requires 304.2640).

8 derivative as illustrated in FIG. 9. Synthesized exactly as found in the general procedure prepared in a manner analogous to 6 (supra); all starting reagents were purchased from Aldrich, Acros, or Sigma: white solid; mp 87–88° C.; $^1$H NMR (CDCl$_3$, 400 MHz) δ 7.16 (t, 1H, J=7.7 Hz), 6.96 (t, 3H, J=6.6 Hz), 5.66 (br, 1H), 5.42 (br, 1H), 2.55 (t, 4H, J=7.8 Hz), 2.19 (t, 2H, J=6.0 Hz), 1.60 (septet, 6H, J=8.0 Hz), 1.37–1.28 (m, 10H), 0.86 (t, 3H, J=6.9 Hz); $^{13}$C NMR (CDCl$_3$, 100 MHz) δ 175.8, 142.8, 142.5, 128.5, 128.0, 125.6, 125.5, 35.92, 35.85, 35.81, 31.7, 31.5, 31.3 29.02 (2), 29.00, 25.3, 22.5, 14.1; IR (film) υ$_{max}$ 3352, 3191, 2925, 2854, 1660, 1630, 1466, 1409, 1341, 1311, 1253, 1202, 1138, 896, 777, 702 cm$^{-1}$; FABHRMS (NBA-NaI) m/z 312.2312 (C$_{19}$H$_{31}$ON+Na$^+$ requires 312.2303).

CH(CH$_3$) derivative as illustrated in FIG. 10. A fresh solution of LDA was prepared at −78° C. under Ar from anhydrous diisopropylamine (0.47 mL, 3.35 mmol, 2.2 eq) and n-BuLi (2.2M in hexanes, 1.4 mL, 3.1 mmol, 2 eq) in anhydrous THF (6 mL). A solution of methyl oleate (0.4556 g, 1.54 mmol, 1 eq) in THF (1 mL) was added dropwise at −78° C. After 50 min of additional stirring, MeI (0.96 mL, 15.4 mmol, 10 eq) was added and the reaction mixture was allowed to warm to 25° C. and stir for 12 h. Saturated aqueous NH$_4$Cl (30 mL) was added to the dark orange solution and the aqueous layer was extracted with EtOAc (3×30 mL). The organic layers were dried (Na$_2$SO$_4$), filtered, and concentrated in vacuo. The crude product was chromatographed (SiO$_2$, 2×15 cm, 0–5% EtOAc/hexanes, gradient elution) to afford α-Me-ester (0.4276 g, 90%) as a clear oil; $^1$H NMR (CDCl$_3$, 500 MHz) δ 5.33–5.30 (m, 2H), 3.64 (s, 3H), 2.40 (s, 1H, J=7.0 Hz), 2.00–1.96 (m, 4H), 1.64–1.60 (m, 1H), 1.39–1.24 (m, 21H), 1.11 (d, 3H, J=7.0 Hz), 0.85 (t, 3H, J=6.8 Hz); $^{13}$C NMR (CDCl$_3$, 125 MHz)

δ 177.4, 130.0, 129.7, 51.4, 39.4, 33.8, 31.9, 29.8, 29.7, 29.5, 29.4, 29.3, 29.1, 27.2, 27.1, 22.7, 17.0, 14.1; IR (film) $\upsilon_{max}$ 2925, 2854, 1741, 1462, 1195, 1157, 723 cm$^{-1}$; FABHRMS (NBA-CsI) m/z 443.1938 ($C_{20}H_{38}O_2$+Cs$^+$ requires 443.1926).

A solution of α-Me-ester (150.5 mg, 0.48 mmol, 1 eq) in THF/MEOH/H$_2$O (3:1:1; 5 mL) was treated with LiOH (67.1 mg, 1.6 mmol, 3.3 eq) and stirred at 25° C. for 15 h. A second portion of LiOH (66.1 mg, 1.58 mmol, 3.3 eq) was added and the reaction was stirred for an additional 7 h. Aqueous HCl (1N, 30 mL) was added and the aqueous layer was extracted with EtOAc (3×30 mL). The organic layers were dried (Na$_2$SO$_4$), filtered, and concentrated in vacuo. The crude product was chromatographed (SiO$_2$, 2×15 cm, 5–20% EtOAc/hexanes, gradient elution) to afford α-Me-acid (111.6 mg, 78%) as a clear oil; $^1$H NMR (CDCl$_3$, 400 MHz) δ 5.37–5.29 (m, 2H), 2.43 (s, 1H, J=6.9 Hz), 1.99 (m, 4H), 1.66 (p, 1H, J=7.2 Hz), 1.43–1.25 (m, 21H), 1.15 (d, 3H, J=7.0 Hz), 0.86 (t, 3H, J=6.8 Hz); $^{13}$C NMR (CDCl$_3$, 125 MHz) δ 183.5, 130.0, 129.7, 39.4, 33.5, 31.9, 29.8, 29.7, 29.5, 29.4, 29.3, 29.1, 27.2, 27.14, 27.10, 22.7, 16.8, 14.1; IR (film) $\upsilon_{max}$ 2925, 2854, 1708, 1466, 1291, 1239, 941, 723 cm$^{-1}$; FABHRMS (NBA-NaI) m/z 297.2797 ($C_{19}H_{36}O_2$+H$^+$ requires 297.2794).

A solution of α-Me-acid (94.4 mg, 0.32 mmol, 1 eq) in anhydrous CH$_2$Cl$_2$ (1.6 mL) under N$_2$ at 0° C. was treated with oxalyl chloride (2M in CH$_2$Cl$_2$, 0.48 mL, 0.96 mmol, 3 eq). The reaction mixture was warmed to 25° C. and stirred for 3 h before the solvent was removed in vacuo. The residue was cooled to 0° C. and treated with excess concentrated NH$_4$OH (1 mL). Water (30 mL) was added and the aqueous layer was extracted with EtOAc (3×30 mL). The organic layers were dried (Na$_2$SO$_4$), filtered, and concentrated in vacuo. The crude product was chromatographed (SiO$_2$, 2×5 cm, 33–50% EtOAc/hexanes, gradient elution) to afford CH(CH$_3$) (70.3 mg, 75%) as a white solid: mp 43–44° C.; $^1$H NMR (CDCl$_3$, 400 MHz) δ 6.20 (br, 1H), 5.59 (br, 1H), 5.33–5.24 (m, 2H), 2.20 (s, 1H, J=6.8 Hz), 1.98–1.93 (m, 4H), 1.61–1.54 (m, 1H), 1.36–1.22 (m, 21H), 1.10 (d, 3H, J=6.9 Hz), 0.83 (t, 3H, J=6.9 Hz); $^{13}$C NMR (CDCl$_3$, 100 MHz) δ 179.7, 129.9, 129.7, 40.8, 34.2, 31.8, 29.7, 29.6, 29.5, 29.2, 29.1, 27.3, 27.13, 27.08, 22.6, 17.7, 14.0; IR (film) $\upsilon_{max}$ 3360, 3186, 2922, 2852, 1654, 1628, 1466, 1414, 1376, 1140, 722, 697 cm$^{-1}$; FABHRMS (NBA) m/z 296.2959 ($C_{19}H_{37}$NO+H$^+$ requires 296.2953).

C(CH$_3$)$_2$ derivative as illustrated in FIG. 9: A fresh solution of LDA was prepared at −78° C. under Ar from anhydrous diisopropylamine (0.20 mL, 1.4 mmol, 2.2 eq) and n-BuLi (2.2M in hexanes, 0.6 mL, 1.3 mmol, 2 eq) in anhydrous THF (2.6 mL). A solution of o-Me-ester (0.2024 g, 0.65 mmol, 1 eq) in THF (0.4 mL) was added dropwise at −78° C. After 50 min of additional stirring, MeI (0.41 mL, 6.6 mmol, 10 eq) was added and the reaction mixture was allowed to warm to 25° C. and stir for 17 h. Saturated aqueous NH$_4$Cl (30 mL) was added and the aqueous layer was extracted with EtOAc (3×30 mL). The organic layers were dried (Na$_2$SO$_4$), filtered, and concentrated in vacuo. The crude product was chromatographed (SiO$_2$, 2×8 cm, 0–5% EtOAc/hexanes, gradient elution) to afford α,α-diMe-ester (170.9 mg, 81%) as a clear oil; $^1$H NMR (CDCl$_3$, 400 MHz) δ 5.34–5.25 (m, 2H), 3.61 (s, 3H), 1.99–1.94 (m, 4H), 1.48–1.44 (m, 2H), 1.27–1.23 (m, 20H), 1.11 (s, 6H), 0.84 (t, 3H, J=6.8 Hz); $^{13}$C NMR (CDCl$_3$, 100 MHz) δ 178.5, 129.9, 129.7, 51.5, 42.2, 40.8, 31.9, 30.0, 29.7, 30 29.6, 29.5, 29.3, 29.1, .27.14, 27.11, 25.1, 24.9, 22.6, 14.0; IR (film) $\upsilon_{max}$ 2926, 2854, 1736, 1464, 1192, 1152 cm$^{-1}$; FABHRMS (NBA-NaI) m/z 325.3101 ($C_{21}H_{40}O_2$+H$^+$ requires 325.3107).

A solution of α,α-diMe-ester (157.6 mg, 0.49 mmol, 1 eq) in THF/MEOH/H$_2$O (3:1:1; 5 mL) was treated with LiOH (408.5 mg, 9.74 mmol, 20 eq) and stirred at 25° C. for 19 h. A second portion of LiOH (408.7 mg, 9.74 mmol, 20 eq) was added and the reaction was stirred for an additional 26 h. A third portion of LiOH (392.0 mg, 9.34 mmol, 19 eq) was added and the reaction was stirred for 47 h at 25° C. and 23 h at 70° C. Aqueous HCl (1N, 30 mL) was added and the aqueous layer was extracted with EtOAc (3×30 mL). The organic layers were dried (Na$_2$SO$_4$), filtered, and concentrated in vacuo. The crude product was chromatographed (SiO$_2$, 2×8 cm, 5–50% EtOAc/hexanes, gradient elution) to afford α,α-diMe-acid (123.4 mg, 82%) as a clear oil; $^1$H NMR (CDCl$_3$, 400 MHz) δ 5.37–5.28 (m, 2H), 2.00–1.97 (m, 4H), 1.53–1.49 (m, 2H), 1.32–1.25 (m, 20H), 1.17 (s, 6H), 0.86 (t, 3H, J=6.8 Hz); $^{13}$C NMR (CDCl$_3$, 100 MHz) δ 185.3, 130.0, 129.8, 42.1, 40.5, 31.9, 30.0, 29.8, 29.7, 29.5, 29.3, 29.1, 27.20, 27.16, 24.9, 24.8, 22.7, 14.1; IR (film) $\upsilon_{max}$ 2925, 2854, 1701, 1467, 1277, 1200, 938 cm$^{-1}$; FABHRMS (NBA-NaI) m/z 333.2778 ($C_{20}H_{38}O_2$+Na$^+$ requires 333.2770).

A solution of α,α-diMe-acid (101.5 mg, 0.33 mmol, 1 eq) in anhydrous CH$_2$Cl$_2$ (1.6 mL) under N$_2$ at 0° C. was treated with oxalyl chloride (2M in CH$_2$Cl$_2$, 0.49 mL, 0.98 mmol, 3 eq). The reaction mixture was warmed to 25° C. and stirred for 3 h before the solvent was removed in vacuo. The residue was cooled to 0° C. and treated with excess concentrated NH$_4$OH (1 mL). Water (30 mL) was added and the aqueous layer was extracted with EtOAc (3×30 mL). The organic layers were dried (Na$_2$SO$_4$), filtered, and concentrated in vacuo. The crude product was chromatographed (SiO$_2$, 2×5 cm, 33–50% EtOAc/hexanes, gradient elution) to afford C(CH$_3$)$_2$ (90.5 mg, 89%) as a white solid: mp 61–62° C.; $^1$H NMR (CDCl$_3$, 400 MHz) δ 6.10 (br, 1H), 5.61 (br, 1H), 5.34–5.26 (m, 2H), 1.97–1.94 (m, 4H), 1.47–1.42 (m, 2H), 1.30–1.23 (m, 20H), 1.13 (s, 6H), 0.84 (t, 3H, J=6.8 Hz); $^{13}$C NMR (CDCl$_3$, 100 MHz) δ 181.0, 129.9, 129.7, 41.9, 41.3, 31.8, 30.0, 29.70, 29.67, 29.5, 29.3, 29.1, 27.2, 27.1, 25.4, 24.7, 22.7, 14.1; IR (film) $\upsilon_{max}$ 3396, 3213, 3002, 2923, 2851, 1650, 1620, 1466, 1401, 1364, 1109 cm$^{-1}$; FABHRMS (NBA-CsI) m/z 310.3115 ($C_{20}H_{39}$NO+H$^+$ requires 310.3110).

"O" derivative as illustrated in FIG. 9 and scheme shown on FIG. 21: Commercially available from Aldrich.

"NH" derivative as illustrated in FIG. 9 and scheme shown on FIG. 21: Commercially available from Aldrich.

CH(SH) derivative as illustrated in FIG. 9 and scheme shown in FIG. 22: A solution of CH(SAc) (72.3 mg, 0.20 mmol, 1 eq) in anhydrous CH$_2$Cl$_2$ (4 mL) under N$_2$ at −78° C. was treated with DIBAL (1M in toluene, 0.61 mL, 0.61 mmol, 3 eq). The reaction mixture was allowed to stir for 1.5 h before a second portion of DIBAL (1M in toluene, 0.61 mL, 0.61 mmol, 3 eq) was added. After 30 min, the reaction was warmed to 25° C. before MeOH (2 mL) and aqueous HCl (5%, 30 mL) were added. The reaction mixture was allowed to stir for 15 min. The aqueous layers were extraced with CH$_2$Cl$_2$ (3×30 mL). The organic layers were dried (Na$_2$SO$_4$), filtered, and concentrated in vacuo. The crude product was chromatographed (SiO$_2$, 1×8 cm, 20–50% EtOAc/hexanes, gradient elution) to afford CH(SH) (31.5 mg, 49%) as a clear oil; $^1$H NMR (CDCl$_3$, 400 MHz) δ 6.22 (br, 1H), 5.46 (br, 1H), 5.37–5.28 (m, 2H), 3.28 (q, 1H, J=6.5 Hz), 2.00–1.91 (m, 4H), 1.74–1.64 (m, 1H), 1.29–1.24 (m, 21H), 0.86 (t, 3H, J=6.8 Hz); $^{13}$C NMR (CDCl$_3$, 100 MHz) δ 175.0, 130.1, 129.7, 43.0, 35.5, 32.0, 29.8, 29.6, 29.5, 29.3, 29.0, 27.2, 27.1, 22.7, 14.1; IR (film) $\upsilon_{max}$ 3363, 3186, 2923, 2853, 2362, 1662, 1458 cm$^{-1}$; FABHRMS (NBA-NaI) m/z 336.2341 ($C_{18}H_{35}$ONS+Na$^+$ requires 336.2337).

CH(SAc): derivative as illustrated in FIG. 9: A solution of Ph$_3$P (182.2 mg, 0.69 mmol, 2 eq) in anhydrous THF (3.5 mL) under N$_2$ at 0° C. was treated with DEAD (110 μL, 0.70 mmol, 2 eq) and allowed to stir for 30 min. Thiolacetic acid (50 μL, 0.70 mmol, 2 eq) was added followed by 2-hydroxy-9Z-octadecenamide (CH(OH); 103.0 mg, 0.35 mmol, 1 eq) in THF (2.2 mL). The reaction mixture was stirred at 0° C. for 2 h before the addition of saturated aqueous NaHCO$_3$ (30 mL). The aqueous layers were extraced with EtOAc (3×30 mL). The organic layers were dried (Na$_2$SO$_4$), filtered, and concentrated in vacuo. The crude product was chromatographed (SiO$_2$, 2×10 cm, 10–50% EtOAc/hexanes, gradient elution) to afford CH(SAc) (96.7 mg, 79%) as a clear oil; $^1$H NMR (CDCl$_3$, 400 MHz) δ 6.12 (br, 1H), 5.63 (br, 1H), 5.35–5.26 (m, 2H), 3.91 (t, 1H, J=7.6 Hz), 2.35 (s, 3H), 2.02–1.90 (m, 5H), 1.67–1.58 (m, 1H), 1.42–1.24 (m, 20H), 0.85 (t, 3H, J=6.9 Hz); $^{13}$C NMR (CDCl$_3$, 100 MHz) δ 196.6, 173.4, 130.0, 129.6, 45.6, 31.9, 30.3, 29.9, 29.7, 29.6, 29.5, 29.3, 29.1, 29.0, 27.2, 27.1, 22.7, 14.1; IR (film) υ$_{max}$ 3448, 3352, 3186, 2923, 2853, 1682, 1457, 1396, 1353, 1259, 1116, 954 cm$^{-1}$; FABHRMS (NBA-NaI) m/z 378.2433 (C$_{20}$H$_{37}$O$_2$NS+Na$^+$ requires 378.2443).

CH(OH) derivative as illustrated in FIG. 9: prepared as previously described (JACS, 1996, 118, 5938–5945).

CHCl derivative as illustrated in FIG. 9: prepared as previously described (JACS, 1996, 118, 5938–5945).

C(=O) derivative as illustrated in FIG. 9: prepared as previously described (JACS, 1996, 118, 5938–5945).

C(=O)CH$_2$ derivative as illustrated in FIG. 9: prepared as previously described (JACS, 1996, 118, 5938–5945).

What is claimed is:

1. A method for potentiating a cell having a serotonin receptor of the subtype 5-HT$_{1A}$, the method comprising the following step:

contacting the cell having the serotonin receptor subtype 5-HT$_{1A}$ with a quantity of a serotonergic agent possessing 5-HT$_{1A}$ agonist activity sufficient for potentiating said cell, said serotonergic agent being selected from the group of compounds represented by the structure:

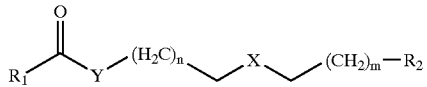

wherein:

X is a diradical selected from the group represented by the following structures:

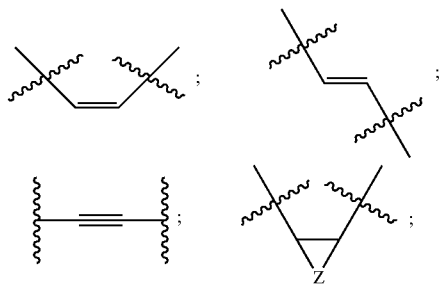

wherein Z is a radical selected from the group consisting of: —CH$_2$—, and —O—;

Y is a diradical selected from the group consisting of: —CH$_2$—, —CH(CH$_3$)—, —C(CH$_3$)$_2$—, —O—, —NH—, —CH (SH)—, —CHSAc)—, —CH (OH)—, —CHCl—, —C(=O)—, —C(=O)CH$_2$—, —CH$_2$NHC(=O)—, and —CH$_2$N(CH$_3$)C(=O)—;

R$_1$ is a radical selected from the group consisting of: hydrogen, —NH$_2$, OH, MeNH—, Me$_2$N—, EtNH—, Et$_2$N—, CH$_2$=CHCH$_2$NH—, n-propyl-NH—, i-propyl-NH—, cyclopropyl-NH—, i-propyl-NMe-, butyl-NH—, pyrrolidine-, phenyl-NH—, phenyl(CH$_2$)$_3$NH—, HONH—, MeONMe-, NH$_2$NH—, CH$_3$O—, CH$_3$CH$_2$O—, CH$_3$(CH$_2$)$_2$O—, Me$_2$CHCH$_2$O—, H—, CF$_3$—, BrCH$_2$—, ClCH$_2$—, N$_2$CH—, HOCH$_2$CH$_2$NH—, (HOCH$_2$CH$_2$)$_2$N—, HOCH$_2$CH$_2$CH$_2$NH—, HOCH$_2$CH(OAc)CH$_2$O—, and HO$_2$CCH$_2$NH—;

R$_2$ is a radical selected from the group consisting of: —CH$_3$, —CH$_2$OCH$_3$, and —CO$_2$H;

n is an integer from 0 to 15; m is an integer from 0 to 15 with the requirement that the sum of n+m is an integer from 11 to 15.

2. A method for potentiating a cell having a serotonin receptor of the subtype 5-HT$_{2A}$, the method comprising the following step:

contacting the cell having the serotonin receptor subtype 5-HT$_{2A}$ with a quantity of a serotonergic agent possessing 5-HT$_{2A}$ agonist activity sufficient for potentiating said cell, said serotonergic agent being selected from the group of compounds represented by the structure:

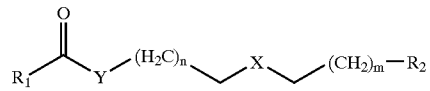

wherein:

X is a diradical selected from the group represented by the following structures:

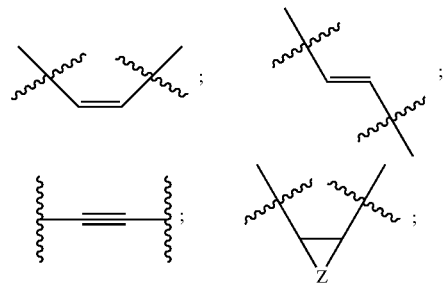

wherein Z is —CH$_2$—;

Y is a diradical selected from the group consisting of: —CH$_2$—, —CH(CH$_3$)—, —O—, —CHCl—, —CH$_2$NHC(=O)—, and —CH$_2$N(CH$_3$)C(=O)—;

R$_1$ is a radical selected from the group consisting of: hydrogen, —NH$_2$, OH, MeNH—, Me$_2$N—, EtNH—, Et$_2$N—, CH$_2$=CHCH$_2$NH—, HONH—, MeONMe-, NH$_2$NH—, CF$_3$—, and ClCH$_2$—

R$_2$ is a radical selected from the group consisting of: —CH$_3$ and —CH$_2$OH;

n is an integer from 0 to 15; m is an integer from 0 to 15 with the requirement that the sum of n+m is an integer from 11 to 15;

with the following proviso:

if Y is CH$_2$, X is an ethene diradical, R$_1$ is —NH$_2$, and R$_2$ is —CH$_3$, then n cannot be 1 if m is 12;

n cannot be 2 if m is 9;

n cannot be 4 if m is 9;

n cannot be 5 if m is 2, 4, 6, 8, 10 and 12;

n cannot be 6 if m is 6;

n cannot be 7 if m is 6; and n cannot be 8 if m is 3.

3. A method for selectively enhancing a serotonergic signal transduction response of a cell having a serotonin receptor of the subtype 5-HT$_{1A}$, the method comprising the following step:

in the presence of serotonin, contacting the cell having the serotonin receptor subtype 5-HT$_{1A}$ with a quantity of a serotonergic agent possessing 5-HT$_{1A}$ agonist activity sufficient for selectively enhancing the serotonergic signal transduction response of said cell, said serotonergic agent being selected from the group of compounds represented by the structure:

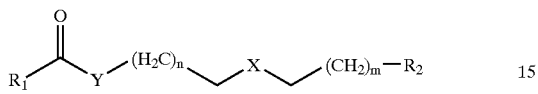

wherein:
X is a diradical selected from the group represented by the following structures:

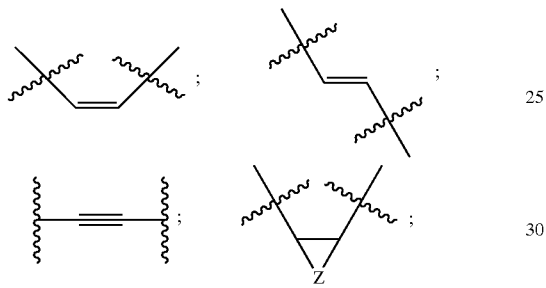

wherein Z is a radical selected from the group consisting of: —CH$_2$ and O;
Y is a diradical selected from the group consisting of: —CH$_2$—, —CH(CH$_3$)—, —C(CH$_3$)$_2$—, —O—, —NH—, —CH(SH)—, —CHSAc)—, —CH(OH)—, —CHCl—, —C(=O)—, —C(=O)CH$_2$—, —CH$_2$NHC(=O)—, and —CH$_2$N(CH$_3$)C(=O)—;
R$_1$ is a radical selected from the group consisting of: hydrogen, —NH$_2$, OH, MeNH—, Me$_2$N—, EtNH—, Et$_2$N—, CH$_2$=CHCH$_2$NH—, n-propyl-NH—, i-propyl-NH—, cyclopropyl-NH—, i-propyl-NMe-, butyl-NH—, pyrrolidine-, phenyl-NH—, phenyl(CH$_2$)$_3$NH—, HONH—, MeONMe-, NH$_2$NH—, CH$_3$O—, CH$_3$CH$_2$O—, CH$_3$(CH$_2$)$_2$O—, Me$_2$CHCH$_2$O—, H—, CF$_3$—, BrCH$_2$—, ClCH$_2$—, N$_3$CH—, HOCH$_2$CH$_2$NH—, (HOCH$_2$CH$_2$)$_2$N—, HOCH$_2$CH$_2$CH$_2$NH—, HOCH$_2$CH(OAc)CH$_2$O—, and HO$_2$CCH$_2$NH—;
R$_2$ is a radical selected from the group consisting of: —CH$_3$, —CH$_2$OCH$_3$, and —CO$_2$H; and
n is an integer from 0 to 15; m is an integer from 0 to 15 with the requirement that the sum of n+m is an integer from 11 to 15.

4. A method for selectively enhancing a serotonergic signal transduction response of a cell having a serotonin receptor of the subtype 5-HT$_{2A}$, the method comprising the following step:

in the presence of serotonin, contacting the cell having the serotonin receptor subtype 5-HT$_{2A}$ with a quantity of a serotonergic agent possessing 5-HT$_{2A}$ agonist activity sufficient for selectively enhancing the serotonergic signal transduction response of said cell, said serotonergic agent being selected from the group of compounds represented by the structure:

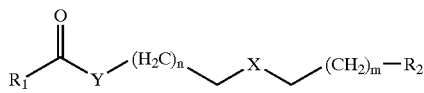

wherein:
X is a diradical selected from the group represented by the following structures:

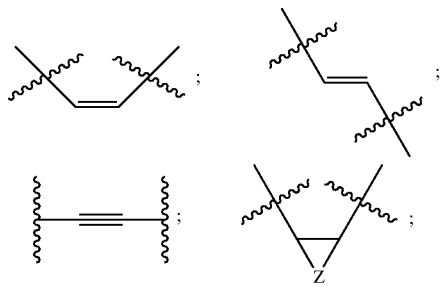

wherein Z is —CH$_2$—;
Y is a diradical selected from the group consisting of: —CH$_2$—, —CH(CH$_3$)—, —O—, —CHCl—, —CH$_2$NHC(=O)—, and —CH$_2$N(CH$_3$)C(=O)—;
R$_1$ is a radical selected from the group consisting of: hydrogen, —NH$_2$, OH, MeNH—, Me$_2$N—, EtNH—, Et$_2$N—, CH$_2$=CHCH$_2$NH—, HONH—, MeONMe-, NH$_2$NH—, CF$_3$—, and ClCH$_2$—;
R$_2$ is a radical selected from the group consisting of: —CH$_3$ and —CH$_2$OH;
n is an integer from 0 to 15; m is an integer from 0 to 15 with the requirement that the sum of n+m is an integer from 11 to 15;
with the following proviso:
if Y is CH$_2$, X is an ethene diradical, R$_1$ is —NH$_2$, and R$_2$ is —CH$_3$, then
n cannot be 1 if m is 12;
n cannot be 2 if m is 9;
n cannot be 4 if m is 9;
n cannot be 5 if m is 2, 4, 6, 8, 10 and 12;
n cannot be 6 if m is 6;
n cannot be 7 if m is 6; and
n cannot be 8 if m is 3.

5. A method for selectively inhibiting a serotonergic signal transduction response of a cell having a serotonin receptor of the subtype 5-HT$_{1A}$ the method comprising the following step:

in the presence of serotonin, contacting the cell having the serotonin receptor subtype 5-HT$_{1A}$ with a quantity of a serotonergic agent possessing 5-HT$_{1A}$ antagonist activity sufficient for selectively inhibiting the serotonergic signal transduction response of said cell, said serotonergic agent being selected from the group of compounds represented by the structure:

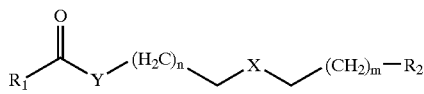

wherein:

X is an ethene diradical;

Y is a methylene diradical;

$R_1$ is a radical selected from the group consisting of: —$NH_2$, and cyclopropyl-NH—;

$R_2$ is a radical selected from the group consisting of: —$CH_3$, —$CH_2OH$, and —$CONH_2$; and n is an integer from 0 to 15; m is an integer from 0 to 15 with the requirement that the sum of n+m is an integer from 11 to 15;

with the following proviso:

if $R_1$ is —$NH_2$, then $R_2$ is not $CH_3$; and if $R_2$ is —$CH_3$, then $R_1$ is $NH_2$.

6. A method for selectively inhibiting a serotonergic signal transduction response of a cell having a serotonin receptor of the subtype 5-$HT_{2A}$, the method comprising the following step:

in the presence of serotonin, contacting the cell having the serotonin receptor subtype 5-$HT_{2A}$ with a quantity of a serotonergic agent possessing 5-$HT_{2A}$ antagonist activity sufficient for selectivly inhibiting the serotonergic signal transduction response of said cell, said serotonergic agent being selected from the group of compounds represented by the structure:

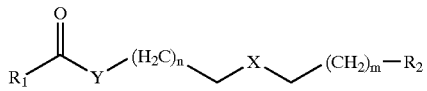

wherein:

X is an ethene diradical;

Y is a diradical selected from the group consisting of: —$CH_2$—, —$C(CH_3)_2$—, —NH—, —CH(SH)—, —CH(SAc)—, —$CH_2NHC(=O)$—, and —$CH_2N(CH_3)C(=O)$—;

$R_1$ is a radical selected from the group consisting of: hydrogen, —$NH_2$, OH, cyclopropyl-NH—, butyl-NH—, phenyl-NH—, $CH_3O$—, $CH_3CH_2O$—, $N_2CH$—, and $HOCH_2CH(OAc)CH_2O$—;

$R_2$ is a radical selected from the group consisting of: —$CH_3$, —$(CH_2)_2CH_3$, —$(CH_2)_4CH_3$, and —$(CH_2)_6CH_3$;

n is an integer from 0 to 15; m is an integer from 0 to 15 with the requirement that the sum of n+m is an integer from 11 to 15;

with the following provisos:

if $R_1$ is —$NH_2$, then Y is not —$CH_2$—; and if Y is —$CH_2$—, then R is not —$NH_2$.

7. A method for selectively potentiating a cell having a serotonin receptor subtype 5-$HT_{1A}$, the method comprising the following step:

contacting the cell having the serotonin receptor subtype 5-$HT_{1A}$ with a serotonergic agent possessing 5-$HT_{1A}$ agonist activity, said serotonergic agent being selected from the group consisting of linoleamide and a compound represented by one of the following structures:

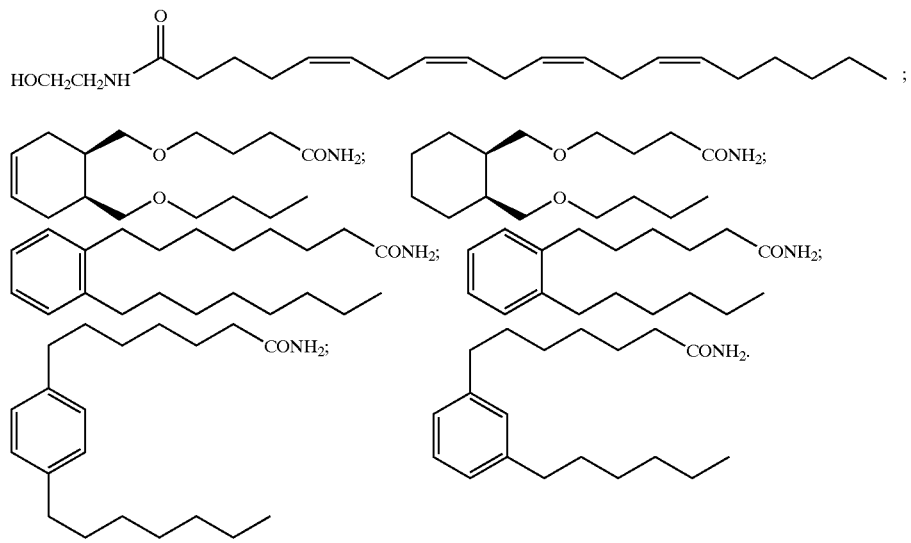

8. A method for selectively potentiating a cell having a serotonin receptor subtype 5-$HT_{2A}$, the method comprising the following step:

contacting the cell having the serotonin receptor subtype 5-$HT_{2A}$ with a serotonergic agent possessing 5-$HT_{2A}$ agonist activity, said serotonergic agent being a fatty acid primary amide selected from the group consisting of $18:2^{9,12}$, $20:2^{11,14}$, $18:3^{6,9,12}$, $18:3^{9,12,15}$, $20:3^{8,11,14}$, $20:3^{11,14,17}$, $20:5^{5,8,11,14,17}$, and $22:6^{4,7,10,13,16,19}$.

9. A method for selectively enhancing a serotonergic signal transduction response of a cell having serotonin receptor subtype 5-$HT_{1A}$, the method comprising the following step:

in the presence of serotonin, contacting the cell having the serotonin receptor subtype 5-$HT_{1A}$ with a serotonergic agent possessing 5-$HT_{1A}$ agonist activity, said serotonergic agent being selected from the group consisting of linoleamide and a compound represented by one of the following structures:

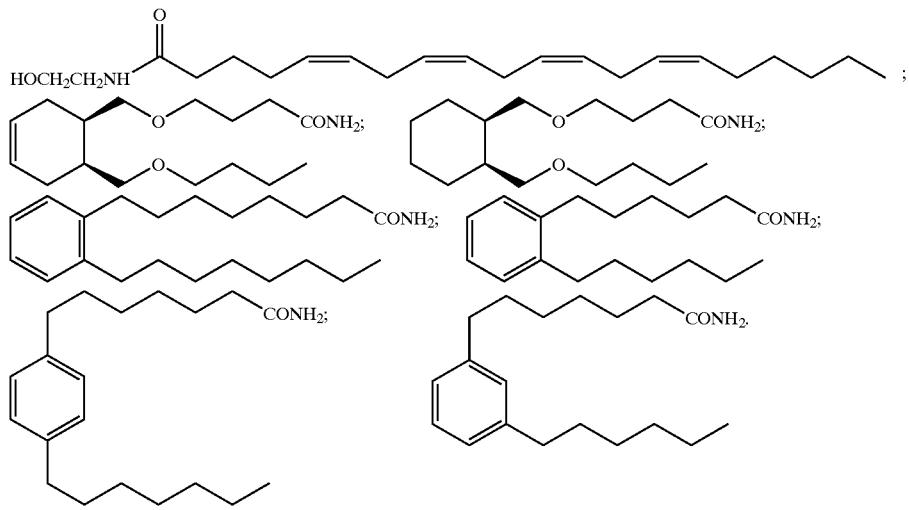

10. A method for selectively enhancing a serotonergic signal transduction response of a cell having serotonin receptor subtype 5-HT$_{2A}$, the method comprising the following step:

in the presence of serotonin, contacting the cell having the serotonin receptor subtype 5-HT$_{2A}$ with a serotonergic agent possessing 5-HT$_{2A}$ agonist activity, said serotonergic agent being a fatty acid primary amide selected from the group consisting of 18:2$^{9,12}$, 20:2$^{11,14}$, 18:3$^{6,9,12}$, 18:3$^{9,12,15}$, 20:3$^{8,11,14}$, 20:3$^{11,14,17}$, 20:5$^{5,8,11,14,17}$, and 22:6$^{4,7,10,13,16,19}$.

* * * * *